United States Patent [19]
Wu et al.

[11] Patent Number: 5,846,705
[45] Date of Patent: Dec. 8, 1998

[54] NUCLEOTIDE SEQUENCE OF TWO CIRCULAR SSDNA ASSOCIATED WITH BANANA BUNCHY TOP VIRUS AND METHOD FOR DETECTION OF BANANA BUNCHY TOP VIRUS

[75] Inventors: Rey-Yuh Wu; Li-Ru You; Tai-Seng Soong, all of Taipei, Taiwan

[73] Assignee: Development Center for Biotechnology, Taipei, Taiwan

[21] Appl. No.: 418,071

[22] Filed: Apr. 6, 1995

[51] Int. Cl.⁶ .............................. C12Q 1/70; C12Q 1/68; C12P 19/34; C07K 13/00
[52] U.S. Cl. .................................. 435/5; 435/6; 435/91.2; 536/23.1; 536/24.3; 536/24.32; 536/24.33; 530/350
[58] Field of Search .................................. 435/6, 5, 91.2; 536/24.3–24.33, 23.1; 530/350

[56] References Cited

PUBLICATIONS

Harding et al. J. of Gen. Virology 74:323–328, 1993.
Erlich et al, PCR Technology; Principles and Applications for DNA Amplification, Publ. Free Mem & Co. pp. 7–31, 1992.
Wu et al, "Purification and Characterization of Banana Bunchy Top Virus", in J. Phytopathology, 128: 153–160 (1990).
Harding et al, "Virus–like particles associated with banana bunchy top disease contain small single–stranded DNA", in J. of General Virology, 72: 225–230 (1991).
Harding et al, "Nucleotide sequence of one component of the banana bunchy top virus genome contains a putative replicase gene", in J. of General Virology, 74:323–328, (1993).
Yeh et al, "Genome Characterization and Identification of Viral–Associated dsDNA Component of Banana Bunchy top Virus", in Virology, 198:645–652 (1994).
Wu et al., (1994) "Nucleotide Sequences Of Two Circular Single–Stranded DNAs Associated With Banana Bunchy Top Virus." 84, 952–958.
R.Y. Wu, "Two Circular Single–Stranded DNAs Associated With Banana Bunchy Top Virus", *J. Phytopathol.*, 142, pp. 292–300 (Nov./Dec. 1994).

*Primary Examiner*—W. Gary Jones
*Assistant Examiner*—Dianne Rees
*Attorney, Agent, or Firm*—Fish & Neave; James F. Haley, Jr.; Margaret A. Pierri

[57] ABSTRACT

Nucleotide sequences of two circular single-stranded DNAs associated with Banana Bunchy Top Virus and the proteins encoded by the open reading frames in the nucleotide sequences are provided. A method for detecting Banana Bunchy Top Virus using the PCR technique based on the nucleotide sequences is also provided.

12 Claims, 20 Drawing Sheets

FIG. 3

```
ATCGGAGATG  GTTTCTAGAT  CTCCAGAACG  CATGAGAATT  GAACAGCCTG

AGATATATCA  CAGATACACA  TCTGTGAAGA  AGTTAAAAAA  ATTCAAGGAG

GAATTCGTTC  ATCCTTGCCT  CGATAGACCA  TGGCAGATTC  AATTGACGGA

GGCAATTGAC  GAGGAACCAG  ATGATCGAAC  GATCTTCTGG  GTCTATGGTC

CGAATGGTAA  TGAGGGGAAA  TCAACATATG  TGAAGTCATT  AATGAAGAAG

GACTGGTTCT  ACACCAGAGG  TGGGAAGAAG  GAGAACG
```

FIG. 7

```
CTTGAACTGG GTACTCCCGGT GGTTCCTGGT TCGAAGAAGC GCAAGCTTCT
CGATAGATTC AGAGAGAGCC CTGAAGAATT GAAGATGGAC GATCCATCCA
AGTATCGCAG ATGCTTGGCA GTGGAATCAA TTAAAGATGC CAGAAATAAT
TCCGAATGGG TTCACGAACT AAAAGAATGG CAAAATAAAT TAATTCAACA
CATCGAAGGT GTTCCCTGATG ATCGAAGTAT CATCTGGGTA TACGGTCCTG
CCGGAGAAGA AGGAAAGTCA ACCTTCGCAA GATATCTATC ATTAAAACCT
```

FIG. 8

```
  1  TATATAAACC GAGGTGGCTT AGTATTACCC ACCTCGGAAC ACTACCCTCTG  50
 51  AACGCCTGGA GATGTCCAGT CCCTCTCTTA AGTGGTGCTT CACTCTGAAT 100
101  TACTCCTCCG CGGCAGAGAG AGAAAACTTT CTCTCTCTTC TGAAGGAGGA 150
151  GGATGTTCAC TACGCTGTCG TCGGCGACGA AGTCGCTCCG GCCACCGGCC 200
201  AGAAGCACCT CCAGGGATAT CTATCCCTGA AAAAGAGAAT CCGCCTCGGC 250
251  GGATTGAAGA AGAAGTATGG TTCCCGTGCT CACTGGGAGA TTGCCAGAGG 300
301  AACGGACGAA GAGAATTCGA AGTACTGTTC AAAAGAAACC CTAATTCTCG 350
351  AATTAGGGTT TCCTGTTGTT AATGGTTCTA ATAAAAGGAA AATATCGGAG 400
401  ATGGTTGCTC GTTCTCCTGA TCGCATGAAA ATTGAACAGC CTGAGATATT 450
451  TCACAGATAT CAATCTGTGA ATAAGTTAAA AAAATTCAAG GAGGAGTTCG 500
501  TTCATCCCTTG CCTCGATAGA CCATGGCAGA TTCAATTGAC GGAGGCAATT 550
551  GACGAGGAAC CCGATGATCG AAGCATCATC TGGGTCTATG GTCCTTATGG 600
```

FIG. 11A

| | | | | | |
|---|---|---|---|---|---|
| 601 | TAATGAGGGT | AAATCAACAT | ATGCGAAGTC | ACTAATCAAG | AAGGATTGGT 650 |
| 651 | TCTACACCAG | GGGTGGGAAG | AAGGAGAATA | TCTTATTCTC | CTATGTGGAC 700 |
| 701 | GAAGGATCTG | ACAAGCATAT | AGTATTTGAT | ATTCCTCGTT | GTAATCAGGA 750 |
| 751 | TTATTTAAAT | TATGATGTAA | TAGAGGCATT | AAAGGATAGG | GTTATAGAGA 800 |
| 801 | GTACTAAATA | CAAACCCATA | AAGATAGTTG | AATTAGGTAA | AATACATGTA 850 |
| 851 | ATCGTCATGG | CGAATTTCAT | GCCTGACTTC | TGTAAAATCT | CCGAAGATCG 900 |
| 901 | AATAAAAATC | ATTTATTGCT | GAAGAACACT | CTATCACGGG | GACACGCTAT 950 |
| 951 | GACAATCGTA | CGCTAAAAAT | CATTATAATT | AATATTTGAA | TTATGGGCCG 1000 |
| 1001 | CAGGCCCCATT | AAGGATGTTC | CGGCCCATTA | ATACGGGCCT | TCGGCCCCGTT 1050 |
| 1051 | ACGCTGAAGT | TGCGCTGAAG | CTTCCTTCGG | AAGATACCTG | GGCGACCTCT 1100 |
| 1101 | GAACGC | | | | 1106 |

*FIG. 11B*

```
2      TATATAAGGA GGAGCGCCTA GTATTACCCG CTCCTCCCTCG CCTTTCCTCC  50
2-17   .......... ......G... .......... ..........  .AC.......

2      TCGCCCCTGA CGTCATCATT ATGTCCTCTT TTAAATGGTG CTTCACTCTG  100
2-17   ....A..... .......... .......... .......... ..........

2      AATTATTCCT CCGCAGCGGA GCGAGAAGAC TTTCTCGCTC TTCTGAAGGA  150
2-17   .......... .......... .......... .......... ..........

2      GGAAGAGTTA AATTACGCTG TCGTCGGGCGA CGAAGTCGCT CCGAGCACCG  200
2-17   ...G..TG.T C.C....T.. .......... .......... ...GC.....

2      GTCGGAAGCA CCTCCAGGGA TATCTATCCC TGAAGAAATC TATTAAGCTT  250
2-17   .C.A...... .......... .......... .....A.... A...CGC..C

2      GGTGGATTGA AGAAGAGGTA CTCTTCGAAG GCTCACTGGG AGAGGGCGAG  300
2-17   ..C....... .A....A... TGGC..CCGT .......... ...TT....A

2      AGGAACTGAT GAACAGAATC GCAGATACTG TTCGAAGGAA ACCC----C  350
2-17   .....G...C .......... .......... .......... ....TAGTT-
```

FIG. 12A

```
     TTGAACTGGG TACTCCGGTG GTTCCTGGTT CGAAGAAGCG CAAGCTTCTC  400
2
2-17 ---------- ---------- ---------- ---------- ----------

GATAGATTCA GAGAGAGCCC TGAAGAATTG AAGATGGACG ATCCATCCAA  450
2
2-17 ---------- -----G---- ---------- ---------- ----------

GTATCGCAGA TGCTTGGCAG TGGAATCAAT TAAAGATGCC AGAAATAATT  500
2
2-17 ---------- ---------- ---------- ---------- ----T-----

CCGAATGGGT TCACGAACTA AAAGAATGGC AAAATAAATT AATTCAACAC  550
2
2-17 ---------- ---------- ---------- ---------- ----------

ATCGAAGGTG TTCCTGATGA TCGAAGTATC ATCTGGGTAT ACGGTCCTGC  600
2
2-17 ---------- ---------- ---------- ---------- -------CAA

CGGAGGCGAA GGAAAGTCAA CCTTCGCAAG ATATCTATCA TTAAAACCTG  650
2
2-17 ---------- ---------- ---------- ---------- -------C--

GATGGGGATA TATCAACGGT GGAAAGACGT CGGATATGAT GCACATCATA  700
2
2-17 ---------- ---------- ---------- ---------- ----------
```

FIG. 12B

```
2    ACGATGGATC CTGATAATCA TTGGATTATT GATATCCCCA GAAGTCATTC  750
2-17 ---------- ---------- ---------- ---------- ----------

2    AGATTATCTG AATTATGGCG TTATAGAACA AATTAAGAAT AGAGTTTTAA  800
2-17 ---------- ---------- ---------- ---------- ----------

2    TAAATACAAA ATACGAACCA TGTGTGATTA GAAAAGATGG ACAAAATGTC  850
2-17 ---------- ---------- ---------- ---------- ----------

2    CATGTAATTG TTATGGCAAA TGTGTTGCCT GATTATTGTA AAATTTCAGA  900
2-17 ---------- ---------- ---------- ---------- ----------

2    AGATAGAATA AAAATAATTA ATTGTTGAGA AAGGAAACTT CCTCCGCAAG  950
2-17 ---------- ---------- ---------- ---------- ----------

2    CAATCAAAAA GCACGTGGAC CCCACACGGT AGCTTGCAGA ACACGCTATC  1000
2-17 ---------- ---------- ---------- ---------- ----------

2    ATTAAATGCA TCAGAAAATC ATTATAATTA ATAAATCTCT TATTGGGCCG  1050
2-17 ---------- ---------- ---------- ---------- ----------

2    CAGGCCCCAT TAAGGCCCAT TACTTAATGG GCCGACCTCC TCGCCC      1096
2-17 ---------- ---------- ---------- ---------- -----A-
```

```
7-4-2:          ---CTTAGTATTAC---
2-17:           ----CTAGTATTAC---
2    :          ---CCTAGTATTACC--
GEMINIVIRUSES:  ----TAATATTAC---
CFDV:           ----TAATACTAG---(+)
                ---CTAGTATTA----(-)
```

FIG. 14

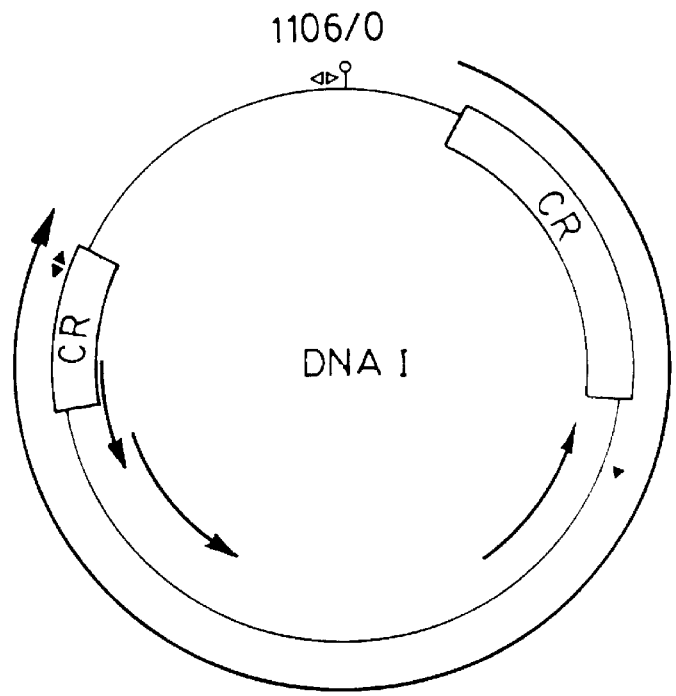
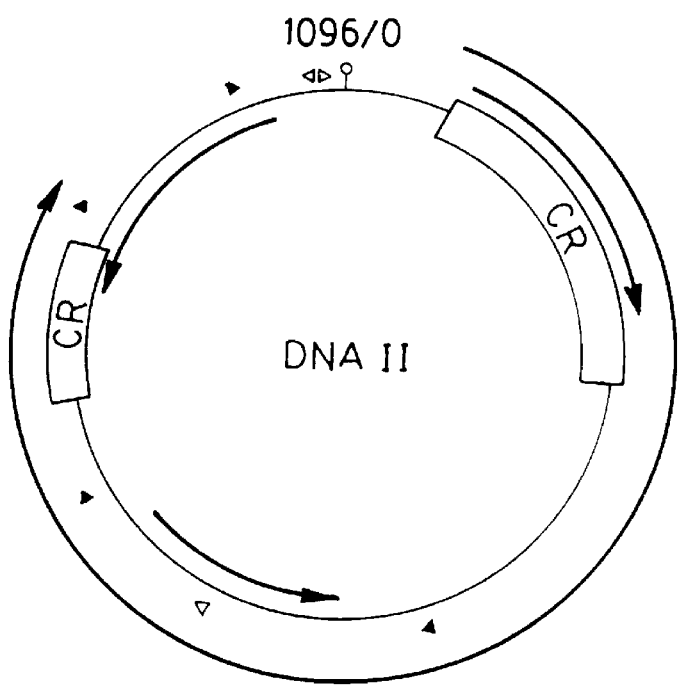
FIG.15

A:    DNAI-V1 (286 AA)

```
  1  MSSPSLKWCF TLNYSSAAER ENFLSLLKEE DVHYAVVGDE VAPATGQKHL QGYLSLKKRI
 61  RLGGLKKKYG SRAHWEIARG TDEENSKYCS KETLILELGF PVVNGSNKRK ISEMVARSPD
121  RMKIEQPEIF HRYQSVNKLK KFKEEFVHPC LDSPWQIQLT EAIDEEPDDR SIIWVYGPYG
181  NEGKSTYAKS LIKKDWFYTR GGKKENILFS YVDEGSDKHI VFDIPRCNQD YLNYDVIEAL
241  KDRVIESTKY KPIKIVELGK IHVIVMANFM PDFCKISEDR IKIIYC
```

B:    DNAII-V2(D2)/BBTV-Component 1(C1) (285/286 AA)

```
        1
D2  MSSFKWCFTL NYSSAAERED FLALLKEEDV HYSVVGDEVA PATGQKHLGG YLSLKK..SI
C1  MARYVVCWMF TINNPTTLPV MRDEIKYKVY QVDRGQEGTR HVQGYVEMKR RSSLKQMRGF

61
D2  RLGG.L.KKK YGSRAHWEIA K.GSDEQNRR YC...SKETL VLELGTPVVP GSKKRKLLDR
C1  FPGAHLEKRK .GSQEEARSY CMKEDTRIEG PEEFGS.FKL SCNDNLFDV. IQDMRETHKR

121
D2  FRE.SPEELK MDDPSKYRRC LAV..ESIKD ARINSEWVHE LKEWQNKLIQ HIEGVPDDRS
C1  PLEYLYDCPN TFDRSKDTLY R.VQAEMNKT KAMNS.WRTS FSAWTSEVEN VMAQ.PCHRR

181
D2  IIWVYGPNGG EGKSTFARYL SLKPGWGYIN GGKTSDMMHI ITMDPDNHWI IDIPRSHSDY
C1  IIWVYGPNGG EGKTTYAKHL MKTRNAFYSP GGKSLDICRL YNYE.DIV.I FDIPRCKEDY

241
D2  LNYGVIEQIK NRVLINTKYE PCVIRKDGQN VHVIVMANVL PDYCKI.SED RIKIINC
C1  LNYGLLEEFK NGIIQSGKYE P.VL.KIVEY VEVIVMANFL PKEG.IFSED RIKLVSC
```

FIG.16

NUCLEOTIDE SEQUENCE OF TWO CIRCULAR SSDNA ASSOCIATED WITH BANANA BUNCHY TOP VIRUS AND METHOD FOR DETECTION OF BANANA BUNCHY TOP VIRUS

FIELD OF INVENTION

The present invention relates to DNA molecules and proteins associated with banana bunchy top virus and a method for detection of banana bunchy top virus.

BACKGROUND OF INVENTION

Banana bunchy top disease (BBTD) is the most important virus disease of banana (particularly *Musa spp.*) in the Eastern Hemisphere. The disease has also been reported for the first time in China, Hawaii and Pakistan.

BBTD is considered to be caused by a possible member of luteovirus based on the disease characteristics, the persistent transmission of the virus by aphids and the induction of phloem damage in infected plants. Numerous attempts to purify banana bunchy top virus (BBTV) have not succeeded due to the presence of latex and phenolic compounds in banana tissues. Purification of BBTV is finally achieved by freezing the diseased tissues in liquid nitrogen to reduce the interference from latex and phenolic compounds before pulverization and solvent extraction, and by stirring and incubating the viral extract at low temperature followed by a cycle of low and high speed centrifugation to remove contaminants as described in Wu et al., 1990, *J. Phytopathol.* 128: 153–160. This procedure has also been successfully applied to isolate BBTV from diseased banana in Australia and Pakistan. The available reports demonstrate that BBTV is an isometric particle having a diameter of 18–20 nm. However, the reported nucleic acids associated with BBTV differ from each other and include ss (single-stranded) RNA as reported in Wu et al., 1990, *J. Phytopathol.* 128:153–160, ssDNA and ssRNA as reported in THOMAS et al., 1991, *J. Gen. Virol.*, 72, 217–224, and ssDNA as reported in HARDING et al., 1991, *J. Gen. Virol.* 72, 225–230.

We have found two different circular single-stranded DNA (cssDNA) associated with BBTV, each with a size of about 1.1 Kb, and have carefully studied the characteristics of the two cssDNA.

SUMMARY OF THE INVENTION

Accordingly, it is an object of the present invention to provide nucleotide sequences, SEQ ID NO. 3 and SEQ ID NO. 4, of two cssDNA molecules associated with BBTV and fragments and variants thereof.

It is another object of the present invention to provide a fragment of DNA molecule having the nucleotide sequence of SEQ ID NO. 1 and a fragment of DNA molecule having the nucleotide sequence of SEQ ID NO. 2 and fragments and variants thereof.

It is further object of the present invention to provide proteins associated with BBTV encoded by the open reading frames in the nucleotide sequences of two cssDNA molecules.

It is yet another object of the present invention to provide a method for detecting BBTV using the polymerase chain reaction (PCR) technique based on the disclosed nucleotide sequences.

BRIEF DESCRIPTION OF THE DRAWINGS

FIG. 3 is a plot of the log of the relative molecular weight ($M_r$) of the BBTV coat protein subunit and marker proteins. Markers and their molecular weight ($M_r$) are as follows: phosphorylase b, 97,400 (A); bovine serum albumin, 68,000 (B); ovalbumin, 43,000 (C); α-chymotrypsinogen, 25,700 (D); β-lactoglobulin, 18,400 (E); and lysozyme, 14,300 (F). The calculated $M_r$ of the BBTV protein subunit is 21,000.

FIG. 7 shows the nucleotide sequence of clone 1 insert which is a subgenomic fragment of BBTV DNA containing 287 base pairs (SEQ ID NO:1 ). Arrows (← →) indicate the position of a pair of oligodeoxynucleotides selected for designation and synthesis of primers for PCR as described in the examples.

FIG. 8 shows partial nucleotide sequence of clone 2 insert which is a second subgenomic fragment of BBTV DNA containing 300 base pairs (SEQ ID NO:2). Arrows (← →) indicate the position of primers designed for PCR using encapsidated DNA template purified by agarose gel electrophoresis as described in the examples.

FIG. 11 shows the nucleotide sequence of BBTV DNA I (Clone 7-4-2) (SEQ ID NO:3) which contains 1106 nucleotides and represents a full length BBTV-DNA synthesized by PCR. Arrows (← →) indicate the stem of the stem-loop structure. An underline (———) shows the starting position of a conserved region.

FIG. 12 shows the nucleotide sequence of BBTV DNA II (Clone 2) (SEQ ID NO:5) which contains 1091 nucleotides and represents a subgenomic DNA of BBTV. Clone 2-17 (SEQ ID NO:4) containing 1096 nucleotides represents a full length BBTV-DNA synthesized by PCR. Stars (*****) indicate the 5 nucleotides lack in clone 2 (SEQ ID NO:5). After adding the five nucleotide to clone 2, a full length BBTV sequence with 1096 nucleotides is obtained (SEQ ID NO:4). Arrows (← →) indicate the stem of the stem-loop structure. An underline (———) indicates the starting position of a conserved region.

FIG. 14 shows the organization of the stem-loop structure in BBTV DNA I (left) and DNA II (right, including clones 2 (SEQ ID NO:5) and 2-17 (SEQ ID NO:4)). The loop sequences of BBTV DNAs are compared with those of geminivirus and CFDV.

FIG. 15 shows the proposed genome organization of BBTV DNA I and DNA II. ORFs on the virion-sense (clockwise) strand and the complementary-sense (anti-clockwise) strand are indicated by arrows. The positions of the stem-loop structure (-o-), conserved region (CR), potential TATA boxes ( ) and poly (A) signals ( ) are also marked.

FIG. 16 shows the predicted amino acid sequence of BBTV DNA I-VI (SEQ ID NO:16) and FIG. 16 shows a comparison between the predicted amino acid sequences of BBTV DNA II-V2 (SEQ ID NO:17) and BBTV-Cl (SEQ ID NO:18).

DETAILED DESCRIPTION OF THE INVENTION

Figure 1:
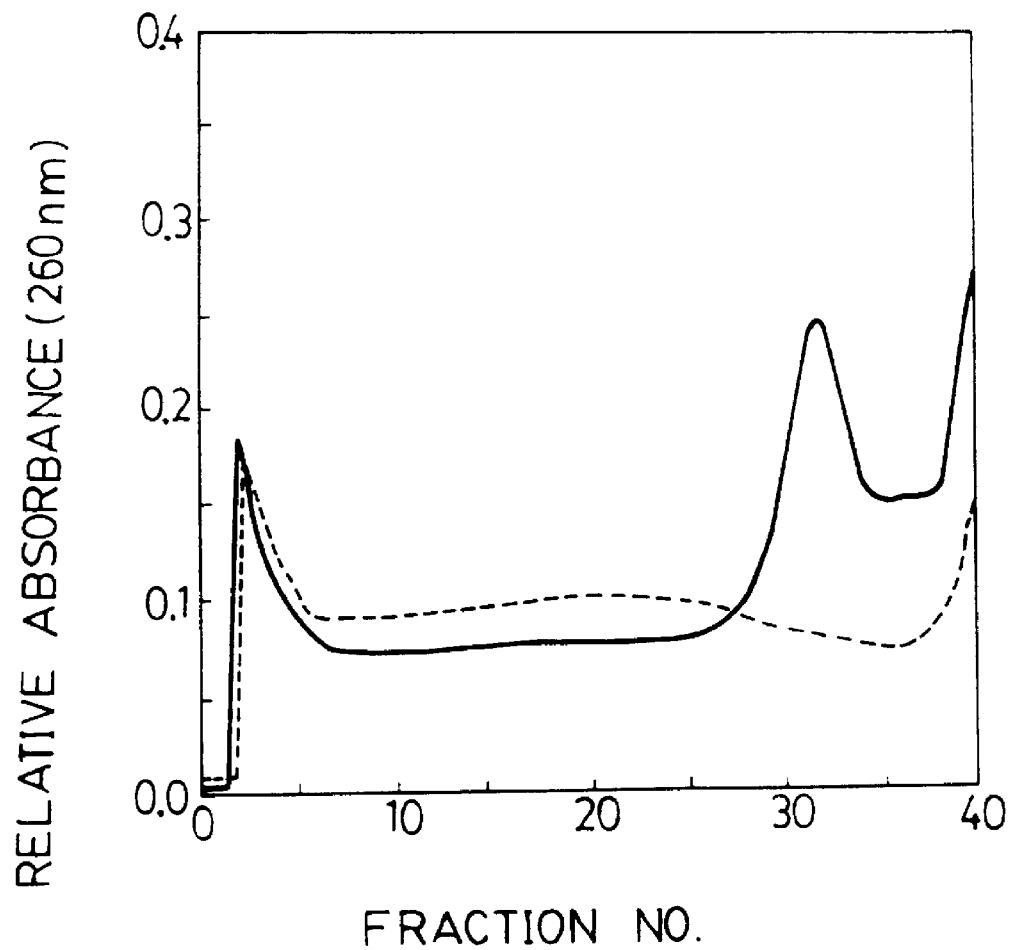
FIG. 1 shows an ultraviolet absorption profile of a purified BBTV preparation (———) as compared with a healthy control ( - - - ).

Banana plants contain considerable amounts of latex and phenolic compounds which may interfere with virus extraction and purification. Pulverization of banana tissues frozen in liquid nitrogen before extraction greatly reduces such interference, and appears to be one of the main factors contributing to the successful extraction and purification of BBTV. Purification is further accomplished by stirring and incubating viral extracts at 4° C. followed by differential centrifugation to remove the contaminants which prevent the detection of BBTV by UV scanning and electron microscope observation.

The virus obtained in this way is the cause of bunchy top disease of banana. The virus is extracted from BBTV-infected plants but not from healthy plants in numerous tests. Similar virus particles are also observed in the phloem parenchyma cells of BBTV-infected plants but not in those of healthy plants. Monoclonal antibodies produced against purified BBTV are able to detect BBTV in (i) crude extract from BBTV-infected plants but not from healthy plants, (ii) viruliferous aphids but not non-viruliferous aphids, and (iii) phloem parenchyma cells of BBTV-infected plants but not of healthy plants.

BBTV particles are hexagonal and 20–22 nm in diameter when observed in the electron microscope, and the virus is considered as a luteovirus. Its calculated A260/280 absorbance ratio is 1.46. The coat protein subunit $M_r$ of BBTV is 21,000.

The virions of BBTV have been shown to consist of at least two different circular single-stranded DNAs, designated as BBTV cssDNA I and BBTV cssDNA II, of about 1.1 Kb. In the present invention, BBTV DNA I and DNA II are found to contain 1106 and 1096 nucleotides, respectively and have the nucleotide sequences of SEQ ID NO. 3 and SEQ ID NO. 4, respectively. The two BBTV DNAs have two conserved regions with more than 80% sequence identity and a stem-loop structure each. These stem-loop structures have a very high sequence homology. BBTV DNA I has four ORFs coding for putative proteins with size of about 33.18, 5.73, 5.54 and 5.41 K, respectively. BBTV DNA II also has four ORFs coding for putative proteins with size of about 6.16, 32.78, 6.55 and 5.66, respectively. As shown in a comparison of the predicted amino acid sequences, one of the open reading frames of BBTV DNA II encodes a replicase.

Among other plant viruses containing cssDNAs, only Geminivirus (Abouzid et al., 1992, *J. Gen. Virol.,* 73:3225–3229 and Dry et al., 1993, *J. Gen. Virol.* 74:147–151) and coconut foliar decay virus (CFDV) (Rohde et al., 1990, *Virology* 176:648–651) have their viral DNA sequenced. BBTV DNAs are smaller than Geminivirus DNAs (1.1 Kb vs 2.6 Kb). These two viruses also have little similarity in nucleotide sequence. However, both viruses contain genomic DNAs which have a stem-loop structure each with highly similar loop sequence and conserved regions in nucleotide sequence. BBTV DNAs seem to have closer relationship with CFDV DNA in loop sequence and size (1.1 Kb vs 1.3 Kb). These two viruses also have sequence similarity (about 39% identity).

We have also developed a sensitive method for detecting the presence of BBTV using polymerase chain reaction (PCR) based on the nucleotide sequence of the two BBTV cssDNA. The method for detecting BBTV in plant tissues comprises:

(1) extracting total DNA of the plant tissues or DNA of viruses contained in the plant tissues;

(2) selecting an inversely oriented primer pair from a nucleotide sequence of SEQ ID NO. 1, 2, 3 or 4;

(3) effecting polymerase chain reaction (PCR) using the extracted DNA as template and the selected primer pair to obtain a PCR product;

(4) detecting the presence of a DNA band of about 1.1 Kb in the PCR product.

In the method, the plant is preferably banana and particularly *Musa spp.*

The ELISA technique has been used to detect the presence of BBTV for years. However, the sensitivity of ELISA in the detection of BBTV is limited by the content of BBTV in the plant tissues. The ELISA technique fails to detect BBTV present in low content. The method for detecting BBTV using the PCR technique as disclosed in the present invention is not significantly limited by the content of BBTV in the plant tissues.

In EXAMPLE 11 below, various kinds of bananas infected with different BBTV were used. BBTV strains S2, S3 and S4 are severe strains but have different symptoms. BBTV strain M1 and M2 are both mild strains. BBTV strain I1 is a strain between mild strain and severe strain. In ELISA method, it is shown that milder strains such as M1, M2 and I1 are hard to be detected, and the optical absorbance value is high only for S4, but is low for all the other isolates including M1, M2, I1 and S2. In contrast, in the PCR method of the present invention using the DNA extracted from the same plant tissue samples, the signals of M1, M2, I1 and S2 strains are as significant as that of S4 strain. Therefore, the method for detecting BBTV of the present invention has higher sensitivity than conventional ELISA method and is particularly useful for detecting BBTV in low content.

The following examples are offered to aid in understanding of the present invention and not to be construed as limiting the scope thereof.

EXAMPLE 1

Purification of Banana Bunchy Top Virus

Petioles, midribs and juvenile leaves of Giant Cavendish banana (*Musa acuminata* Colla.) seedlings naturally infected with BBTV were collected from banana plantations in southern Taiwan. Small pieces (ca. 15×15 mm) of diseased leaf tissues were placed in liquid nitrogen for 1 min and pulverized in a coffee grinder for 1 min. The powder (1 g/2 ml) was mixed with 0.1M potassium phosphate buffer, pH 7.4, containing 0.2% (v/v) 2-mercaptoethanol and 0.1% (w/v) sodium diethyldithiocarbamate and stirred at 10° C. for 30 min. The mixture was filtered through two layers of cheesecloth and chloroform: n-butanol (1:1) was added gradually to 10% (v/v). The mixture was emulsified for 1 h with a magnetic stirrer, incubated for 10 min at 4° C. and centrifuged at 7,000 rpm for 10 min. The supernatant was centrifuged in a Beckman 45 Ti rotor at 36,000 rpm for 2.5 h and the resulting pellet was resuspended in 0.07M phosphate buffer, pH 7.2. The suspension was stirred for 2 days, then stored for 2 days at 4° C. The suspension was subsequently clarified by low speed centrifugation at 7,000 rpm for 10 min and the virus was concentrated by high speed centrifugation at 36,000 rpm for 2.5 h. The pellet was resuspended in 0.07M phosphate buffer, pH 7.2 (2 ml per 100 g tissue). The virus was further purified by sucrose density gradient centrifugation (2.5–30% w/v) in a Beckman SW 28-1 rotor at 26,000 rpm for 3.5 h. The tube contents were fractioned and collected with a fraction collector. Ultraviolet absorption at 260 nm of each fraction was determined with a spectrophotometer and those containing virus were pooled, diluted with three volumes of 0.07M phosphate buffer, pH 7.2, centrifuged at 36,000 rpm for 3 h and the pellet was resuspended in the same buffer (1/600 volume of the original extract). The ultraviolet absorption spectrum (200–400 nm) of the virus preparation was made in a spectrophotometer. The virus concentrations in purified preparations were estimated using an extinction coefficient ($E_{260}^{0.1\ \%}$) of 8.6.

After the extract of BBTV-infected plants was processed through one cycle of differential centrifugation, a small peak was detected at fraction no. 30 upon UV scanning of sucrose density gradient columns. The peak was not present in UV absorption profile of similarly treated extracts of healthy plants.

When the virus-containing extract was further purified by stirring and incubating for 2 days each at 4° C. followed by a second cycle of differential centrifugation, a distinct peak appeared in fractions no. 28–35 (FIG. 1). These fractions contained numerous uniform virus particles which were hexagonal in outline and approximately 20–22 nm in diameter. There was no peak in the UV absorption profile of healthy plant extract, nor were there hexagonal particles in its fractions no. 28–35.

When leaf blades and midribs plus petioles of BBTV-infected seedlings were extracted and purified, the concentrations of BBTV obtained were 0.34 and 0.56 mg/kg tissues, respectively. From April 1986 to May 1987 BBTV-infected leaves were collected from banana plantations at least once a month, and the concentrations of BBTV in the tissue were determined. Healthy leaves were used as controls. The virus concentration was highest (up to 0.64 mg/kg tissue) in BBTV-infected leaves collected from October to December. An average of 0.15 mg BBTV/Kg tissue was detected in diseased leaves collected in April and May, and about 0.05 mg BBTV/Kg tissue was obtained from diseased leaves collected from January to March. All these preparations contained numerous virus particles when observed in the electron microscope. Although the amount of virus could not be determined because of the inconspicuous nature of the peak in UV absorption profiles, some virus particles were observed in the preparations from diseased leaves collected from June to September. Virus particles were not detected in any of the healthy leaves tested. When purified BBTV preparation was negatively stained with 2% uranyl acetate, the virus particles were 20–22 nm in diameter. Some of them appeared hexagonal. Upon closer examination, coat protein subunits and capsid cores of the virus particles were also visible. When virus preparation was stored at −20° C. for 12 h before being negatively stained with 2% uranyl acetate, the virus particles formed aggregates and measured 20 nm in diameter.

The UV absorbance profile of BBTV was characteristic of a nucleoprotein, having a maximum absorbance at 257 nm, a minimum absorbance at 240 nm and a A260/280 nm ratio of 1.46.

EXAMPLE 2

Preparation of Coat Protein Subunit of Banana Bunchy Top Virus

The relative molecular weight ($M_r$) of BBTV coat protein subunits was determined by SDS-12% polyacrylamide gel electrophoresis using the system of LAEMMLI as described in Nature, Lond. 1970, 227, 680–685. Samples were prepared by the addition of an equal volume of 2 X "treatment buffer" consisting of 0.125M Tris-Cl, pH 6.8, 4% (w/v) sodium dodecyl sulphate, 20% (v/v) glycerol, 10% (v/v) 2-mercaptoethanol, 10M urea, and 0.001% bromophenol blue, to either BBTV or standard protein solutions (Bio-Rad Laboratories, Rockville Center, N.Y.) followed by incubation in boiling water for 3 min. Electrophoresis of samples was carried out in a dual slab cell (Bio-Rad Laboratories, Richmond, Calif.). The gels were stained in a solution consisting of 0.25% Coomassie brilliant blue, 10% (v/v) acetic acid and 50% (v/v) methanol, and destained in a solution of 7% (v/v) acetic acid and 10% (v/v) methanol. The $M_r$ of BBTV coat protein was estimated by interpolation from plots of the $M_r$ of the standard proteins against their relative mobilities in the gel. Standard proteins and their $M_r$ were: lysozyme, 14,300; β-lactoglobulin, 18,400; α-chymotrypsinogen, 25,700; ovalbumin, 43,000; bovine serum albumin, 68,000; phosphorylase b, 97,400; myosin (H-chain), 200,000.

Figure 2:
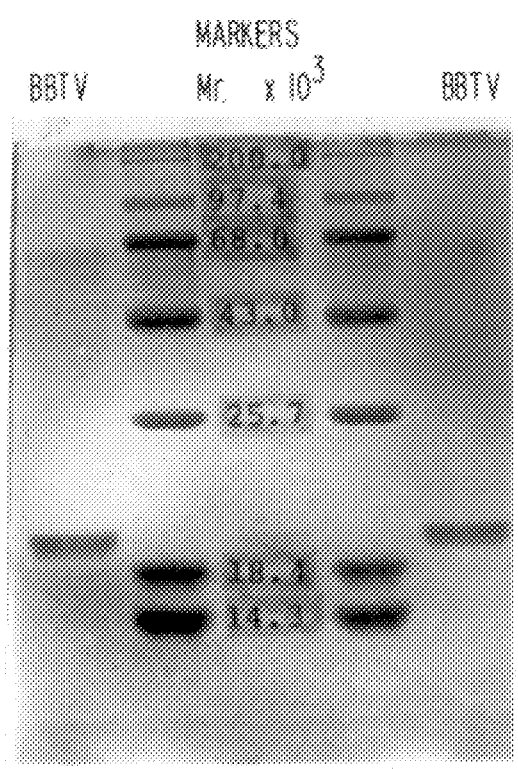
FIG. 2 shows an electrophoresis pattern of BBTV protein subunits and marker proteins in 12% SDS polyacrylamide gel.
Figure 3:
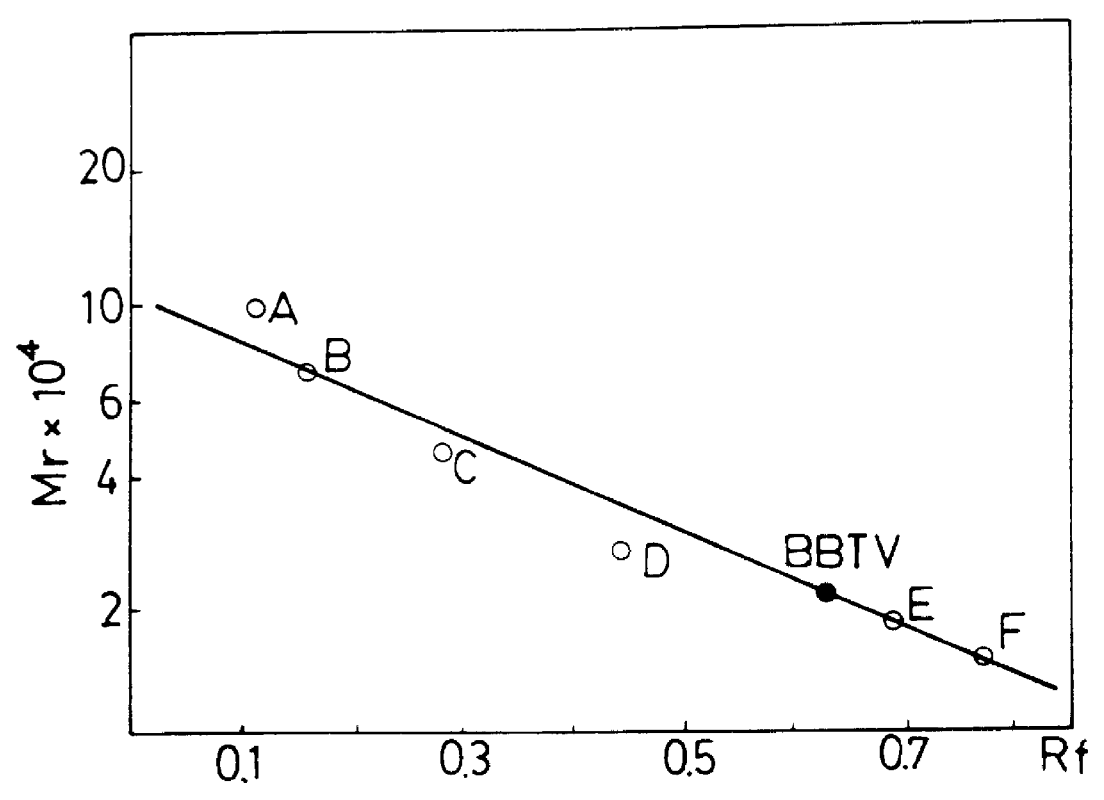

After dissociation and electrophoresis of BBTV, the viral protein showed a single major band with a Rf value between that of β-lactoglobulin and α-chymotrypsinogen (FIGS. 2 and 3). The calculated $M_r$ of BBTV protein subunit was 21,000.

EXAMPLE 3

Isolation of Banana Nucleic Acid

BBTV-infected or healthy banana tissues was ground to a powder after dipping in liquid nitrogen, and the powdered tissue from 1 g tissue was mixed with 15 ml of extraction buffer (0.1M Tris-HCl, 0.5 M NaCl, 0.05M EDTA and 0.01M 2-mercaptoethanol, pH 8.0) and 2 ml of 10% SDS. The mixture was incubated at 65° C. for 12 min before the addition of 5 ml of 5M potassium acetate, incubated in ice for 30 min and clarified by centrifugation at 13,000 g for 30 min. The nucleic acid in the supernatant was precipitated with an equal volume of isopropanol and collected by centrifugation at 13,000 g for 30 min. The pellet was resuspended in 700 Al Tris-EDTA buffer (50 mM Tris-HCl and 10 mM EDTA, pH 8.0). DNA was further purified by digesting the suspension with RNase A (15 µg/ml) and proteinase K (140 µg/ml) at 37° C. for 90 min. The mixture was extracted with phenol-chloroform and chloroform, precipitated with ethanol, and resuspended in 50 µl of sterile distilled water.

EXAMPLE 4

Isolation and Characterization of BBTV Nucleic Acid

Purified BBTV in 0.07M sodium phosphate buffer, pH 7.2, was mixed with ⅓ volume of 4X disruption buffer which contained 4% SDS, 80 MM $Na_2HPO_4$, 40 MM $NaH_2PO_4$, 4 mM EDTA and 4% 2-mercaptoethanol. After incubation at 60° C. for 15 min, the mixture was extracted twice with equal volume of phenol, once each with phenol-chloroform and chloroform, and the nucleic acids were precipitated with ethanol and resuspended in sterile distilled water as described by HARDING et al., 1991, *J. Gen. Virol.* 72, 225–230. To determine the nature of BBTV nucleic acid, preparations were treated at 37° C. for 1 hr with (i) DNase [50 µg/ml, Boehringer Mannheim (BM)] in 50 mM Tris-HCl, 10 mM $MgCl_2$, pH 8.0, (ii) RNase (50 µg/ml, BM) in water or (iii) nuclease S1 (1 unit/µl, BM) in 0.2M NaCl, 50 mM sodium acetate, and 1 mM $ZnSO_4$, pH 4.5, and subjected to electrophoresis in horizontal 1.2% agarose gels in Tris-borate-EDTA buffer, pH 8.3 as described in MANIATIS et al., 1982, *Molecular cloning: A Laboratory Manual.* New York: Cold Spring Harbor Laboratory.

To eliminate external nucleic acids, purified BBTV was incubated at 37° C. for 1 h with DNase (50 µg/ml, BM) and RNase (50 µg/ml, BM). BBTV nucleic acids were isolated from the treated BBTV preparations and analyzed as described above. BBTV nucleic acid was labelled with $^{32}p$ at the 3' end using terminal transferase (BM). BBTV DNA (1 µg) was added with terminal transferase buffer (0.2M potassium cacodylate, 25 mM Tris-HCl, 0.25 mg/ml BSA, pH 6.6), 2.5 mM $CoCl_2$, 50 µCi [$\alpha^{32}p$] ddATP, and 25 units of terminal transferase, then incubated at 37° C. for 1 h to label the 3' end of BBTV DNA. The mixture was then subjected to electrophoresis in 1% agarose alkaline gel, stained with ethidium bromide, and autoradiographied as described in MANIATIS et al., 1982, *Molecular cloning: A Laboratory Manual.* New York: Cold Spring Harbor Laboratory.

Figure 4:
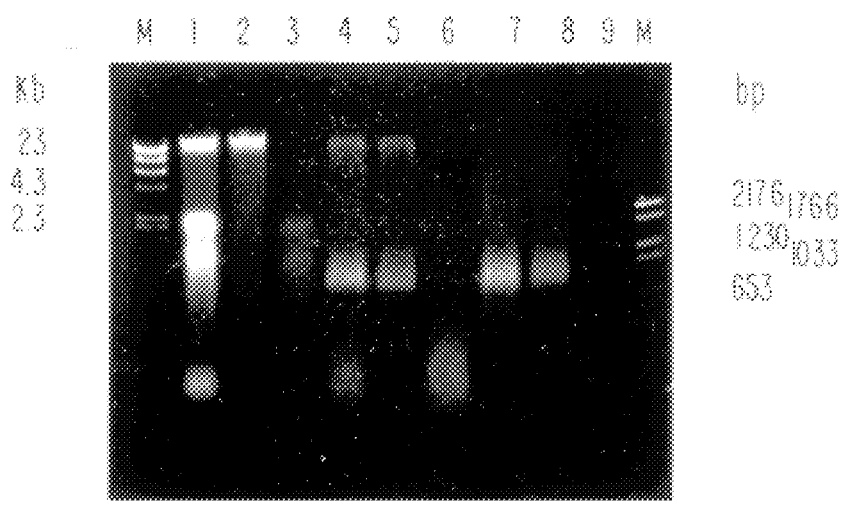
FIG. 4 shows an agarose gel electrophoresis pattern of nucleic acids isolated from healthy banana tissues and different BBTV preparations. The samples analyzed in the electrophoresis are as follows: DNA size markers (lane M), nucleic acids isolated from healthy banana tissues before (lane 1) and after treatment with RNase (lane 2) and DNase (lane 3), from sucrose density-purified BBTV before (lane 4) and after treatment with RNase (lane 5) and DNase (lane 6), and from BBTV treated with DNase and RNase prior to phenol extraction (lane 7) and after further treatment with RNase (lane 8) and DNase (lane 9).

When nucleic acids isolated from partially purified BBTV were subjected to electrophoresis, three discrete bands of c. 20 Kb, 0.9–1.1 Kb and 0.3 Kb were observed (FIG. 4). The 20 Kb and 0.9–1.1 Kb bands were sensitive to digestion by DNase but not to RNase, while the 0.3 Kb band was sensitive to digestion by RNase but not to DNase (FIG. 4). BBTV preparations pretreated with DNase and RNase to eliminate external nucleic acids before disruption, yield only the 0.9–1.1 Kb nucleic acids. No corresponding DNA band was observed in total nucleic acid isolated from healthy banana tissues which, like partially purified BBTV, contained 20 Kb DNA and 0.3 Kb RNA (FIG. 4). This 0.9–1.1 Kb band was sensitive to digestion by DNase (FIG. 4) and S1 nuclease (data not shown), but not to RNase (FIG. 4) or to restriction enzymes including Bam HI, Dra I, Eco RI, Hind III, Hpa II, Pru II, Pst I, Sac I, Sma I and Sna BI (data not shown). These results indicated that encapsidated BBTV nucleic acid is a single-stranded DNA (ssDNA).

Figure 5:
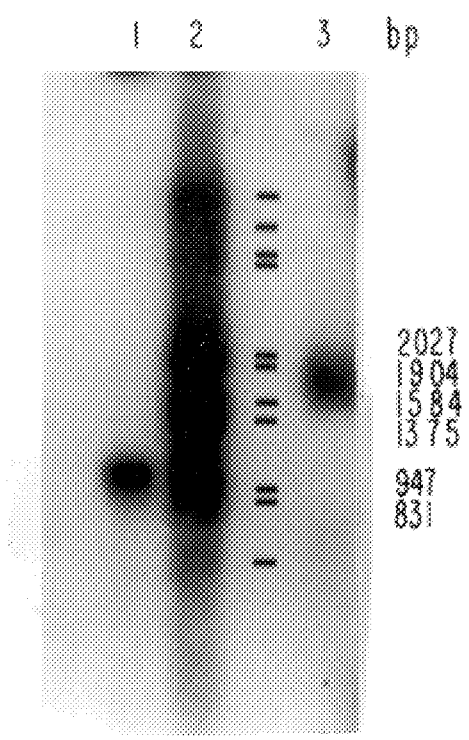
FIG. 5 shows an autoradiogram of the [α-$^{32}$P]-labelled BBTV-DNA (labelled at 3' end with terminal transferase) (lane 1), BBTV-cDNA synthesized using the random primer technique (lane 3) and [α-$^{32}$P]-labelled DNA markers (lane 2) on an alkaline agarose gel.
Figure 6:
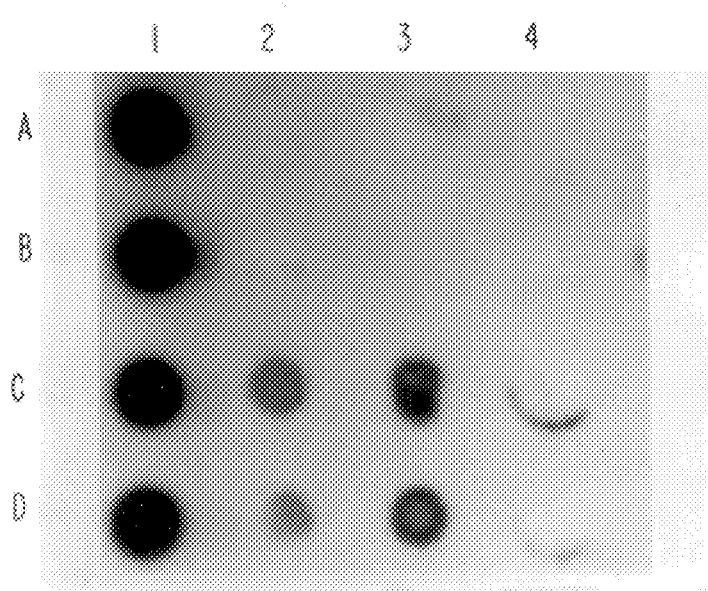
FIG. 6 shows the results of a dot blot analysis confirming the identity of BBTV clone 2. The DNAs blotted on nylon membrane are from four BBTV-infected banana plants and six healthy banana plants (A2, B2; A3, B3; A4, B4; A5, B5; C4, D4; C5, D5). Two of the four BBTV-infected banana plants show severe symptoms (A1, B1; C1, D1) and the other two show mild symptoms (C2, D2; C3, D3). The probe used in the hybridization is DIG-labelled probe 2.
Figure 9A:
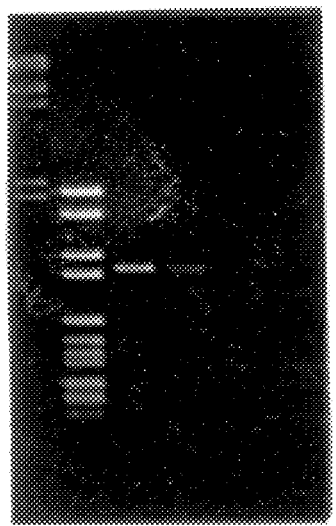
FIGS. 9A and B show an agarose gel analysis pattern of DNA fragments amplified by PCR. A: oligonucleotides designated BB-1 (SEQ ID NO:6) and BB-3 (SEQ ID NO:7) are used as primers [(-) sense, CATGGTCTATCGAG-GCAAGG; (+) sense, GCAGATTCAATTGACGGAGG]. The samples applied in the gel are as follows: DNA size markers (lanes A1 and A2) and DNA fragments amplified by PCR using DNA of encapsidated BBTV (lane A3) and cellular DNA from BBTV-infected banana (lane A4) as template. B: oligonucleotides designated 2-2 (SEQ ID NO:8) and 2-3 (SEQ ID NO:9) are used as primers [(-) sense, ACCACCGGAGTACCCAGTTC; (+) sense, TCCTGGTTCGAAGAAGCGCA]. The samples applied in the gel are as follows: DNA size markers (lanes B1 and B4) and DNA fragments amplified by PCR using DNA of encapsidated BBTV (lane B2) and cellular DNA from BBTV-infected banana (lane B3) as template.
Figure 9B:
Figure 10A:
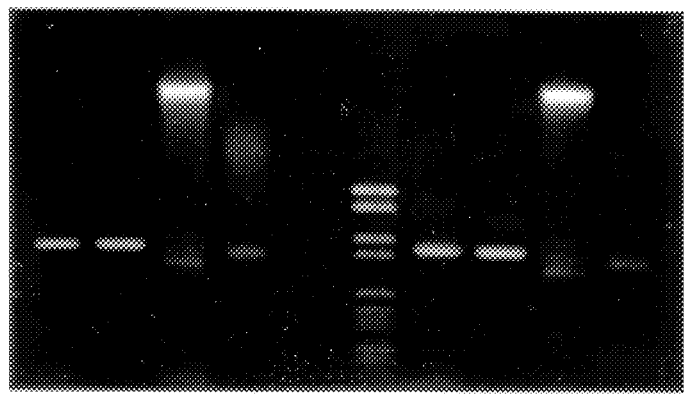
FIGS. 10A and B show the patterns of agarose gel electrophoresis (A) and Southern hybridization analysis (B) comparing the two PCR products (PCR 1 and PCR 2, as shown in FIGS. 9A and 9B, respectively) with the encapsidated BBTV-DNA and cellular DNA from diseased tissues. In electrophoresis, DNAs are separated on 1.2% agarose gel and visualized with ethidium bromide staining. The DNAs are transferred to a nylon membrane (Hybone-N, Promega) after photographing, and hybridized with digoxigenin-labelled BBTV-cDNA probe 1 (B left) and probe 2 (B right), respectively. The samples applied in the gel are as follows: PCR 1 products (lanes 1 and 6) amplified using the BB-1 (SEQ ID NO:6) and BB-3 (SEQ ID NO:7) primer pair and encapsidated BBTV-DNA template; PCR 2 products (lanes 2 and 7) amplified using the 2-2 (SEQ ID NO:8) and 2-3 (SEQ ID NO:9) primer pair and encapsidated BBTV-DNA template; total DNA (lanes 3 and 8) purified from BBTV-infected banana tissues and encapsidated BBTV-DNA (lanes 4 and 9); and DIG-labelled DNA size markers (BM) (lane 5).
Figure 10B:
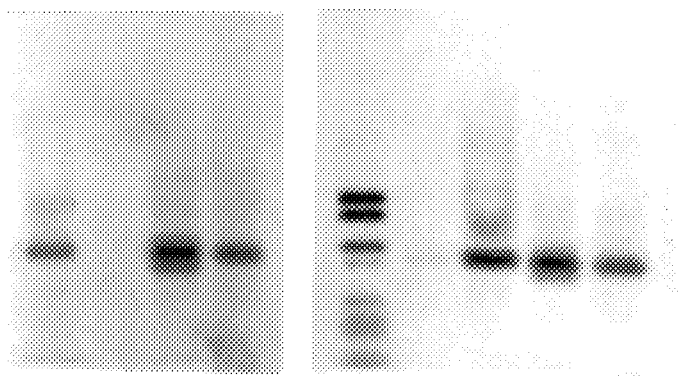

BBTV DNA was radio-labelled with $^{32}p$ using terminal transferase (FIG. 5), results suggesting the possibility of the existence of a 3' end on BBTV DNA. However, cloning the BBTVcDNA by tailing the 3' end with poly d(A) and synthesizing cDNA with poly d(T) as a primer were unsuccessful (data not shown). On the other hand, the synthesized cDNAs of BBTV were c. 1.8–2.0 Kb (FIG. 5) which are larger than the original template of 0.9–1.1 Kb, results suggesting that the DNA template is circular.

EXAMPLE 5

BBTV DNA Cloning

For cloning of BBTV cDNA, the synthesized complementary DNAs of BBTV were linearized and blunt-ended by treatment with mung bean nuclease (BM) and ligated into pGEM 7zf (+) plasmid vector which has been digested with Sma I (BM). The plasmid was then used to transform *E. coli* strain JM 109 and the potential recombinant clones were identified by screening on X-gal substrate.

Plasmids were isolated by the alkaline lysis method as described in MANIATIS et al., 1982, *Molecular Cloning: A Laboratory Manual.* New York: Cold Spring Harbor Laboratory, and the inserts were excised by digestion with Eco RI and Hind III. After separation by agarose electrophoresis, the DNAs were transferred to a nylon membrane followed by Southern hybridization as described in SOUTHERN et al., 1975, *J. Mol. Biol.*, 98, 503–517 with the $^{32}$P-labelled BBTV-DNA probe to confirm the identity of the BBTV clones.

The BBTV-DNA probes were prepared by treatment of synthesized BBTV cDNA with mung bean nuclease to make blunt-ended dsDNA followed by ligation with Uni-Amp adaptor (Clontech Lab.) and amplification with PCR using the Uni-Amp primer (Clontech Lab.) and [$\alpha^{32}$P] DATP as a marker.

Figure 13A:
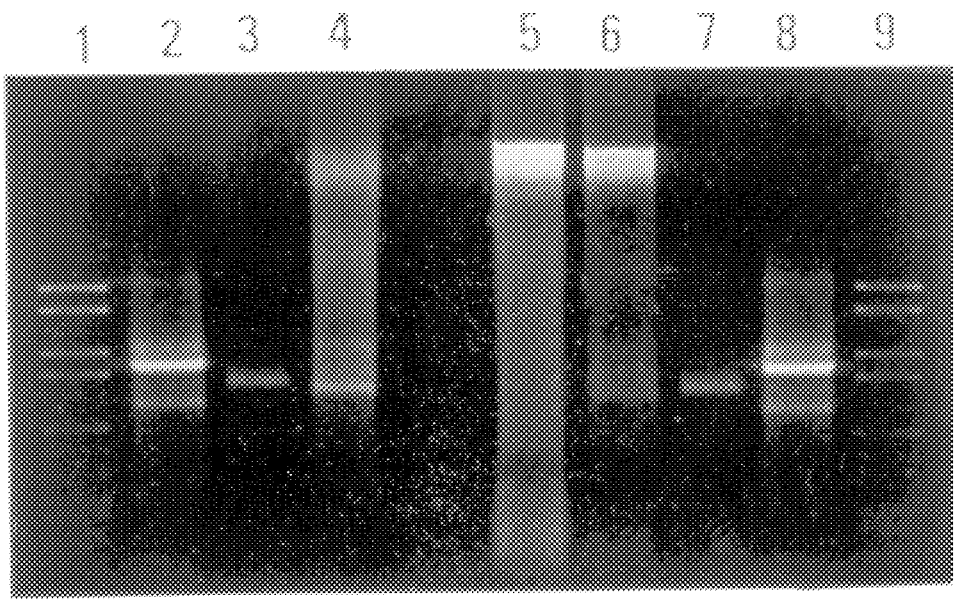
FIG. 13 shows the patterns of agarose gel electrophoresis and Southern hybridization analysis determining the sequence orientation of BBTV cssDNA. The samples applied to the gel are as follows: encapsidated BBTV-DNA (lanes 3 and 7), total DNA extracted from BBTV-infected tissues (lanes 4 and 6), total DNA extracted from healthy tissues (lane 5), PCR products amplified using BB-1 (SEQ ID NO:6) and BB-2 (SEQ ID NO:12) primers (lanes 2 and 8), and DNA size markers labelled with digoxigenin (lanes 1 and 9). The DNAs are separated on 1.2% agarose gel and visualized with ethidium bromide staining (A). The DNAs are transferred to a nylon membrane after photographing, and hybridized with probe C1 (SEQ ID NO:10)(B left) and probe C2 (SEQ ID NO:11)(B right), respectively.
Figure 13B:
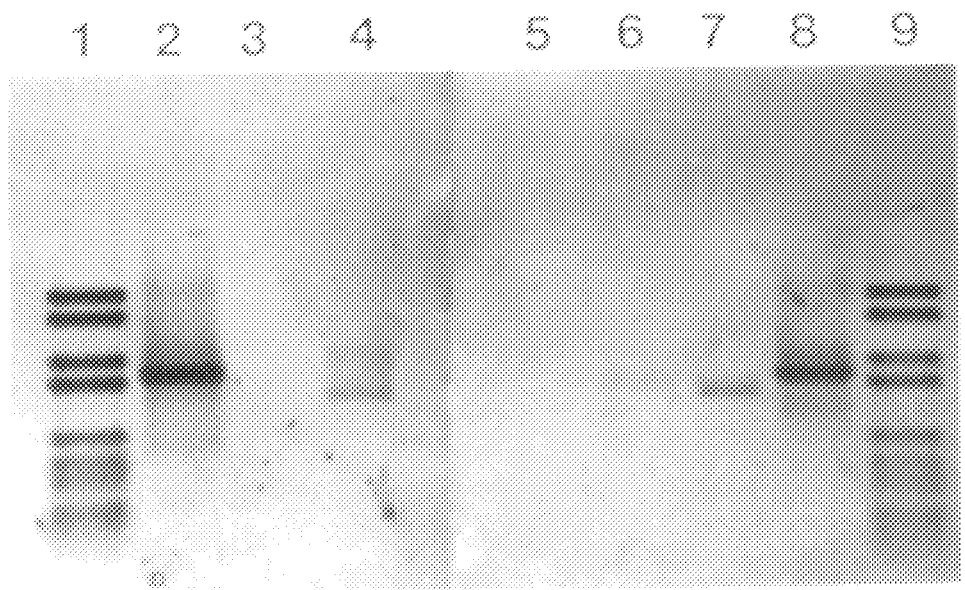
Figure 17:
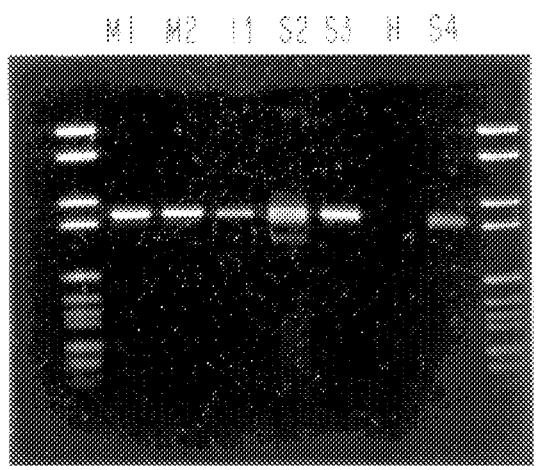
FIG. 17 shows the agarose gel electrophoresis pattern comparing the PCR products amplified using BB-1 (SEQ ID NO:6) and BB-3 (SEQ ID NO:7) as primer pair and the DNAs extracted from healthy and diseased tissues as template. DNAs are separated on 1.2% agarose gel and visualized with ethidium bromide staining. The sample applied in lane 1 of the gel is DNA size markers (BM). The samples applied in lanes 2, 3, 4, 5, 6, 7 and 8 of the gel are the PCR amplification products using DNAs of M1, M2, I1, S2, S4, S3 BBTV strains and total DNAs of diseased banana tissues and healthy banana tissues as template respectively.

Of several BBTV DNA clones that were obtained two, referred to as clones 1 and 2 (SEQ ID NO:1 and SEQ ID NO:2, respectively), were selected for sequence analysis. Their DNAs were used as templates to synthesize clone 1 and clone 2 digoxigenin-labelled DNA probes (DIG-probes, DIG DNA labelling and detection kit with experimental procedures were supplied by Boehringer Mannheim Co.), respectively. Both probes hybridized with total DNA isolated from BBTV-infected banana tissues but not with that from healthy banana tissues. The dot blot result of DIG-probe 2 is shown in FIG. 6.

EXAMPLE 6

Sequencing of BBTV DNA Clones

The nucleotide sequences of BBTV cDNA clones were determined by the chain-termination DNA sequencing method as described in SANGER et al. 1977, *Proc. Natl. Acad. Sci. U.S.A.* 74, 5463–5467, using the United States Biochemical Corporation Sequenase Version 2.0 DNA sequencing Kit. Double-stranded plasmid DNAs were used as templates and Sp6/T7 were used as sequencing primers.

Clone 1 consisted of 287 nucleotides shown in FIG. 7 (SEQ ID NO:1) and clone 2 contained a 1.0 Kb DNA insert with its partial nucleotide sequence shown in FIG. 8 (SEQ ID NO:2).

EXAMPLE 7

PCR Using Clones 1 and 2 Primers

The polymerase chain reaction (PCR) was performed in 100 $\mu$l volumes in a Perkin Elmer/Cetus Thermal Cycler, using Tag DNA polymerase (Clontech Lab.) and reaction conditions provided by Perkin-Elmer/Cetus [10 mM Tris-HCl, 50 mM KCl, 1.5 MM $MgCl_2$, 0.001% (w/v) gelatin, 0.2 mM of each dNTP, 30 p mole of each primer]. The reagent mixture was heated at 72° C. for 7 min and subjected to 25 cycles of amplification (1 min at 94° C., 2 min at 45° C., 3 min at 72° C.). After PCR reaction, the mixture was loaded onto 1.5% agarose gel for electrophoresis analysis.

To verify the circular nature of BBTV DNA, two pairs of primers each pair in opposite directions were designed according to the nucleotide sequences of clones 1 and 2 (SEQ ID NO:1 and SEQ ID NO:2). The pair of clone 1 primers designated BB-1 (SEQ ID NO:6) and BB-3 (SEQ ID NO:7) containing CATGGTCTATCGAGGCAAGG, and GCAGATTCAATTGACGGAGG, respectively. The clone 2 primer pair designated 2-2 (SEQ ID NO:8) and 2-3 (SEQ ID NO:9) has the nucleotide sequence of ACCACCGGAGTACCCAGTTC and TCCTGGTTCGAAGAAGCGCA, respectively. When purified BBTV DNA or total DNA from diseased banana tissues was used as template in PCR using BB-1 and BB-2 or 2-2 and 2-3 primers, each generated a DNA product of 1.1 Kb (FIG. 9), results suggesting that the BBTV DNA templates are circular and c. 1.1 Kb.

To compare the PCR products obtained from two different primer pairs, a Southern hybridization test was conducted. PCR products synthesized with clone 1 (SEQ ID NO:1) primers were hybridized strongly with clone 1 probe but weakly with clone 2 probe, while those synthesized with clone 2 (SEQ ID NO:2) primers were hybridized strongly with clone 2 probe but not with clone 1 probe (FIG. 10). Probes to both clones 1 and 2 hybridized strongly with encapsidated BBTV DNA and DNA isolated from BBTV-infected banana respectively (FIG. 10). Thus, at least two species of circular single-stranded DNAs (cssDNA) are probably associated with BBTV. The cssDNAs containing the nucleotide sequences of clones 1 and 2 were designated BBTV cssDNA I and BBTV cssDNA II, respectively.

EXAMPLE 8

DNA Sequence Analysis

Base sequences of BBTV DNA clones were determined by the dideoxynucleotide chain termination method, using the United States Biochemical Corporation Sequenase Version 2.0 DNA Sequencing Kit. SP6 and T7 primers were purchased from Promega Company, and other synthetic oligonucleotide primers were synthesized by Kwai Shin Company (Taiwan) using Cruachem DNA synthesizer PS 250. Comparative analysis of BBTV sequence was done using MacMolly computer software package (Soft Gene Gmbh, Germany) and PC/GENE sequence analysis package (Intelligenetics Inc.)

Several clones representing different circular DNA of BBTV were obtained. Base sequences of clones 7-4-2 (SEQ ID NO:3) and 2-17 (SEQ ID NO:4) representing the full length clones of BBTV DNA I and DNA II, respectively, were analyzed. The clone 7-4-2 which represented the BBTV DNA I PCR product was completely sequenced in both directions and was found to contain 1106 nucleotides as shown in FIG. 11.

The clone 2-17 (SEQ. ID NO:4) which represented the BBTV DNA II PCR product was also completely sequenced in both directions and found to contain 1096 nucleotides as shown in FIG. 12. In comparison with the BBTV-cDNA clone 2 (SEQ ID NO:5) that contained 1091 nucleotides, the PCR clone 2-17 consisted of 5 more nucleotides (from position 345 to 349 of clone 2-17) that were absent in BBTV-cDNA clone 2. Therefore, the sequence of BBTV DNA II could be obtained by combining the whole 1091 nucleotides of BBTV-cDNA clone 2 with 5 nucleotides (TAGTT) of clone 2-17 (PCR product), resulting in a total of 1096 nucleotides.

EXAMPLE 9

Determination of the Sense Strand in the Virion

After the nucleotide sequences of two DNAs of BBTV were determined and two conserved regions in BBTV-DNA were found, two oligonucleotides (C1: TGGTGCTTCACTCTGAATTACTCCTCCGCG (SEQ ID NO:10); C2, with complementary sequence of C1: CGCGGAGGAGTAATTCAGAGTGAAGCACCA (SEQ ID NO:11)) were designed and synthesized, based on 30 nucleotide in the starting position of conserved region (position 83-112 on DNA 1). The two oligonucleotides were labelled by digoxigenin (dig) using the DNA 3' end-labelling kit (Boehringer Mannheim). Encapsidated DNA of BBTV, PCR products obtained by using encapsidated DNA of BBTV as template and BB-1 (SEQ ID NO:6) and BB-2 (SEQ ID NO:12) (CGAGATTCAAGACGGA) as primers, and total DNA from banana tissues were subjected to electrophoresis in 1.2% agarose and transferred to Hybond-N membrane (Promega Co.) followed by southern hybridization with dig-labelled C1 or C2 probes. The hybridization was conducted at 68° C. for 15 hr in buffer containing 5xSSC, 1% blocking reagent (from B. M.), 1% SDS and DNA probe. Results showed that C2 (SEQ ID NO:11) probe hybridized encapsidated DNA but C1 (SEQ ID NO:10) probe did not, although C1 probe hybridized the PCR product from BB-1 (SEQ ID NO:6) and BB-2 (SEQ ID NO:12) primers and total DNA from diseased banana tissues as C2 probe did (FIG. 13). This results also confirm the sequence presented in FIGS. 11 and 12 was the orientation present in virion.

Both BBTV DNAs I and II are circular and each has one stem-loop structure. In DNA I, the sequence CCGAGGTGG is inversely repeated (FIG. 11 arrow <—— ——>) and seems to form a stable stem structure (FIG. 14) with loop sequence of CTTAGTATTAC (SEQ ID NO:13). The stem sequence (AGGAGGAGCG) (SEQ ID NO:14) in DNA II was different from that (CCGAGGAGG) in DNA I but the two stem loop structures have very high homology with only one base difference in loop sequence (FIG. 14). The nucleotide 1 position is determined based on their stem-loop structure in both DNAs. The two BBTV DNAs have two conserved regions (CRs) with more than 80% sequence identity. The first CR which contained 208 nucleotides was located on position 83 to 290 of BBTV DNA I (clone 7-4-2)(SEQ ID NO:3), but was located on position 86 to 293 of BBTV DNA II (clone 2)(SEQ ID NO:5). In this CR the sequence identity between clone 7-4-2 and clone 2 was 82%, while that between clone 7-4-2 and clone 2-17 (SEQ ID NO:4) was 92%. The second CR which contained 78 nucleotides was located on position 845 to 922 of BBTV DNA I (clone 7-4-2) and on position 851 to 928 of BBTV DNA II (clone 2). They have 82% sequence identity.

EXAMPLE 10

Determination of Open Reading Frames (ORF) in the DNA Associated with BBTV

The open reading frames (ORFs) were identified in both BBTV DNA I (clone 7-4-2) (SEQ ID NO:3) and DNA II (clone 2 plus 5 nucleotides)(SEQ ID NO:4), in (+) sense and complementary strands. ORFs with the potential to encode proteins of $M_r$ greater than 5K in BBTV DNA I and DNA II are shown in FIG. 15A and Table 1, and FIG. 15B and Table 2, respectively.

TABLE 1

Open reading frames of BBTV DNA I (SEQ ID NO:3)

| ORF* | nucleotide start | stop | protein $M_r^+$ |
|---|---|---|---|
| V2 | 62 | 920 | 33184 |
| C1 | 779 | 638 | 5733 |
| C3-1 | 912 | 762 | 5535 |
| C3-2 | 426 | 282 | 5407 |

*V and C indicate virion-sense and complementary-sense ORFs respectively.
+Size of putative translation products.

TABLE 2

Open reading frames of BBTV DNA II (SEQ ID NO:4)

| ORF* | nucleotide start | stop | protein $M_r^+$ |
|---|---|---|---|
| V1 | 85 | 244 | 6164 |
| V2 | 71 | 926 | 32783 |
| C2-1 | 1059 | 885 | 6550 |
| C2-2 | 699 | 546 | 5661 |

*V and C indicate virion-sense and complementary-sense ORFS, respectively.
+Size of putative translation products.

In BBTV DNA I (SEQ ID NO:3), there are one ORF in virion sense (V2) and three in the complementary sense (C1, C3-1, C3-2) for encoding the putative viral proteins with sizes ranging from 5.4 to 33.18 K. The largest ORF V2 has 858 nucleotides (starting from 62 to 920) that codes for a 33.18K protein. One TATA box promoter element (TATATAA) was located at the bottom of stem of stem-loop structure (from 1 to 7 nt) in BBTV DNA I. Two poly (A) signal (AATAAA) were present in position 380-385 and 901-906 (FIGS. 11 and 15A).

In BBTV DNA II (SEQ ID NO:4), there are two ORFs in virion sense (V1, V2) and two in complementary sense (C2-1, C2-2) for encoding putative viral proteins with sizes ranging from 5.6 to 32.78K. The largest ORF V2 has 855 nucleotides (starting from 71 to 926) that codes for a 32.78K protein. One TATA box potential promoter element (TATATAA) was located at the bottom of the stem structure (from 1 to 7 nt) and one closely related sequence element (GATATATC) was located at position 657 to 664. Four poly(A) signal (AATAAA) were present in position 533 to 538, 799 to 804, 907 to 912 and 1030 to 1035 (FIGS. 12 and 15B).

Alignment of these two sequences with published Geminivirus and CFDV DNA sequences using PC/GENE sequence analysis package (Intelligenetics Inc.) show no close sequence relationship between BBTV and Geminivirus, but some similarity (about 39% identity) between BBTV DNA II and the reported sequence of CFDV DNA. In Geminiviruses, the conserved region starts from the stem of stem-loop structure, while in BBTV DNA the conserved region did not start from stem of stem-loop structure but from position 86. However, the nucleotide sequences of the loop in both BBTV DNAs (CTTAGTATTAC and CCTAGTATTACC) (SEQ ID NO:13 and SEQ ID NO:15, respectively) do have some similarity with that of Geminivirus (TAATATTAC) and CFDV [(+) TAATACTAG/ (-) CTAGTATTA].

The predicted amino acid sequences of ORF-V1 (FIG. 16A) in DNA I and ORF-V2 in DNA II were compared with ORF-V1 in BBTV-C1. DNA II-V2 had some identical amino acids as BBTV-C1-V1 and consisted of a NTP-binding motif G(GE)GKS (starting at a. a. position 178) proposed to be associated with virus replicase (FIG. 16B).

EXAMPLE 11

Detection of BBTV By Polymerase Chain Reaction (PCR) and Enzyme-linked Immunosorbent Assay (ELISA)

1. Preparation of BBTV DNA and total banana DNA and detection of BBTV by PCR

Various kinds of bananas infected with different BBTV were used. BBTV strains S2, S3 and S4 are all severe strains but have different symptoms. BBTV strain S2 was collected from the farm of the National Taiwan University, Taiwan, and BBTV strains S3 and S4 were both collected from Ping-Dong, Taiwan, but at different time. BBTV strains M1 and M2 are both mild strains but have different symptoms. They are available from the Department of Phytopathology of the National Taiwan University. BBTV strain I1 is a strain between mild strain and severe strain and was collected from the Department of Phytopathology of the National Taiwan University. Total banana DNA was prepared as described in EXAMPLE 3 and BBTV DNA were prepared as described in EXAMPLE 4.

The pair of primers designated BB-1 (SEQ ID NO:6) and BB-3 (SEQ ID NO:7) respectively containing CATGGTCTATCGAGGCAAGG, and GCAGATTCAAT-TGACGGAGG was used in the PCR reactions. The PCR was performed in 100 μl volumes in a Perkin Elmer/Cetus Thermal Cycler, using Tag DNA polymerase (Clontech Lab.) and reaction conditions provided by Perkin-Elmer/Cetus [10 mM Tris HCl, 50 mM KCl, 1.5 mM $MgCl_2$, 0.001% (w/v) gelatin, 0.2 mM of each dNTP, 30 p mole of each primer]. The reagent mixture was heated at 72° C. for 7 min and subjected to 25 cycles of amplification (1 min at 94° C., 2 min at 45° C., 3 min at 72° C.). After PCR reaction, 5 μl of the reaction mixture was loaded onto 1% agarose gel for electrophoresis to determine the existence of DNA bands and the size of DNA molecules.

The DNAs extracted from BBTV strains isolated from banana tissues of various symptoms were used as templates. All consistently produced a single band of about 1.1 Kb after PCR amplification using BB-1 and BB-3 as primer pair, while the DNA extracted from healthy banana tissues produce no corresponding band (FIG. 16). The result indicates that the PCR detection method is specific to the DNA extracted from banana tissues suffering with BBTD and can be used to detect the presence of BBTV.

2. Preparation of BBTV proteins and total banana proteins and detection of BBTV by ELISA Banana tissues infected with BBTV was treated with liquid nitrogen followed by pulverized in a pulverizer. The pulverized tissues was then extracted with 0.1M K-P buffer containing 0.1% Na-DIECA and 0.2 α-mercaptoethanol. The extract was centrifuged at 8,000 rpm for 10 minutes. The supernatant was used as antigen. Antibody trap ELISA (direct ELISA) was performed by coating antibody against BBTV on ELISA plate, subjecting the supernatant prepared to the plate for trapping BBTV antigen, subjecting BBTV antibodies conjugated with alkali phosphatase to the plate, adding the substrate of alkali phosphatase to the plate for color development, and then determining the optical absorption at 405 nanometer ($A_{405}$) in an ELISA reader.

The optical absorbance data are shown in Table 3. The optical absorption is high only in S4 strain but is low in strains M1, M2, I1 and S2. The result indicates that the content of BBTV is high in banana tissues infected with S4 strain and is low in banana tissues infected with all the other strains. ELISA detection method fails to detect the presence of BBTV in low content.

TABLE 3

ELISA detection of BBTV

| ELISA | (A405) |
|---|---|
| M1 | 0.121 |
| M2 | 0.292 |
| I1 | 0.112 |
| S2 | 0.246 |
| S4 | 1.197 |
| H | 0.048 |

It will be appreciated that modifications of the above examples may be readily made by those skilled in the art. We, therefore, intend by the appended claims to cover the modifications alluded to herein as well as all other modifications which fall within the true spirit and scope of our invention.

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 287 base pairs
        ( B ) TYPE: nucleic acid
        ( C ) STRANDEDNESS: single
        ( D ) TOPOLOGY: linear ( i i ) MOLECULE TYPE: subgenomic DNA
        ( A ) DESCRIPTION: /desc= "clone 1 insert"

( i i i ) HYPOTHETICAL: NO ( i v ) ANTI-SENSE: NO ( v ) ORIGINAL SOURCE:
        ( A ) ORGANISM: Banana Bunchy Top Virus (BBTV)

( x i ) SEQUENCE DESCRIPTION: SEQ ID NO:1:

| | | | | | |
|---|---|---|---|---|---|
|ATCGGAGATG|GTTTCTAGAT|CTCCAGAACG|CATGAGAATT|GAACAGCCTG|AGATATATCA|60|
|CAGATACACA|TCTGTGAAGA|AGTTAAAAAA|ATTCAAGGAG|GAATTCGTTC|ATCCTTGCCT|120|
|CGATAGACCA|TGGCAGATTC|AATTGACGGA|GGCAATTGAC|GAGGAACCAG|ATGATCGAAC|180|
|GATCTTCTGG|GTCTATGGTC|CGAATGGTAA|TGAGGGAAA|TCAACATATG|TGAAGTCATT|240|
|AATGAAGAAG|GACTGGTTCT|ACACCAGAGG|TGGGAAGAAG|GAGAACG| |287|

(2) INFORMATION FOR SEQ ID NO:2:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: subgenomic DNA
        (A) DESCRIPTION: /desc= "partial clone 2 insert"

(iii) HYPOTHETICAL: NO (iv) ANTI-SENSE: NO (vi) ORIGINAL SOURCE:
        (A) ORGANISM: Banana Bunchy Top Virus (BBTV)

(xi) SEQUENCE DESCRIPTION: SEQ ID NO:2:

| | | | | | |
|---|---|---|---|---|---|
|CTTGAACTGG|GTACTCCGGT|GGTTCCTGGT|TCGAAGAAGC|GCAAGCTTCT|CGATAGATTC|60|
|AGAGAGAGCC|CTGAAGAATT|GAAGATGGAC|GATCCATCCA|AGTATCGCAG|ATGCTTGGCA|120|
|GTGGAATCAA|TTAAAGATGC|CAGAAATAAT|TCCGAATGGG|TTCACGAACT|AAAAGAATGG|180|
|CAAAATAAAT|TAATTCAACA|CATCGAAGGT|GTTCCTGATG|ATCGAAGTAT|CATCTGGGTA|240|
|TACGGTCCTG|CCGGAGAAGA|AGGAAAGTCA|ACCTTCGCAA|GATATCTATC|ATTAAAACCT|300|

(2) INFORMATION FOR SEQ ID NO:3:

(i) SEQUENCE CHARACTERISTICS:
        (A) LENGTH: 1106 base pairs
        (B) TYPE: nucleic acid
        (C) STRANDEDNESS: single
        (D) TOPOLOGY: circular (ii) MOLECULE TYPE: genomic DNA
        (A) DESCRIPTION: desc= "BBTV DNA I (clone 7-4-2)"

(iii) HYPOTHETICAL: NO (iv) ANTI-SENSE: NO (vi) ORIGINAL SOURCE:
        (A) ORGANISM: Banana Bunchy Top Virus (BBTV)

(xi) SEQUENCE DESCRIPTION: SEQ ID NO:3:

| | | | | | |
|---|---|---|---|---|---|
|TATATAAACC|GAGGTGGCTT|AGTATTACCC|ACCTCGGAAC|ACTACCTCTG|AACGCCTGGA|60|
|GATGTCCAGT|CCCTCTCTTA|AGTGGTGCTT|CACTCTGAAT|TACTCCTCCG|CGGCAGAGAG|120|
|AGAAACTTT|CTCTCTCTTC|TGAAGGAGGA|GGATGTTCAC|TACGCTGTCG|TCGGCGACGA|180|
|AGTCGCTCCG|GCCACCGGCC|AGAAGCACCT|CCAGGGATAT|CTATCCCTGA|AAAAGAGAAT|240|
|CCGCCTCGGC|GGATTGAAGA|AGAAGTATGG|TTCCCGTGCT|CACTGGGAGA|TTGCCAGAGG|300|
|AACGGACGAA|GAGAATTCGA|AGTACTGTTC|AAAAGAAACC|CTAATTCTCG|AATTAGGGTT|360|
|TCCTGTTGTT|AATGGTTCTA|ATAAAAGGAA|AATATCGGAG|ATGGTTGCTC|GTTCTCCTGA|420|
|TCGCATGAAA|ATTGAACAGC|CTGAGATATT|TCACAGATAT|CAATCTGTGA|ATAAGTTAAA|480|
|AAAATTCAAG|GAGGAGTTCG|TTCATCCTTG|CCTCGATAGA|CCATGGCAGA|TTCAATTGAC|540|

-continued

```
GGAGGCAATT GACGAGGAAC CCGATGATCG AAGCATCATC TGGGTCTATG GTCCTTATGG      600
TAATGAGGGT AAATCAACAT ATGCGAAGTC ACTAATCAAG AAGGATTGGT TCTACACCAG      660
GGGTGGGAAG AAGGAGAATA TCTTATTCTC CTATGTGGAC GAAGGATCTG ACAAGCATAT      720
AGTATTTGAT ATTCCTCGTT GTAATCAGGA TTATTTAAAT TATGATGTAA TAGAGGCATT      780
AAAGGATAGG GTTATAGAGA GTACTAAATA CAAACCCATA AAGATAGTTG AATTAGGTAA      840
AATACATGTA ATCGTCATGG CGAATTTCAT GCCTGACTTC TGTAAAATCT CCGAAGATCG      900
AATAAAAATC ATTTATTGCT GAAGAACACT CTATCACGGG GACACGCTAT GACAATCGTA      960
CGCTAAAAAT CATTATAATT AATATTTGAA TTATGGGCCG CAGGCCCATT AAGGATGTTC     1020
CGGCCCATTA ATACGGGCCT TCGGCCCGTT ACGCTGAAGT TGCGCTGAAG CTTCCTTCGG     1080
AAGATACCTG GGCGACCTCT GAACGC                                          1106
```

( 2 ) INFORMATION FOR SEQ ID NO:4:

( i ) SEQUENCE CHARACTERISTICS:
        ( A ) LENGTH: 1096 base pairs
        ( B ) TYPE: nucleic acid
        ( C ) STRANDEDNESS: single
        ( D ) TOPOLOGY: circular ( i i ) MOLECULE TYPE: genomic DNA
        ( A ) DESCRIPTION: /desc "BBTV DNA II (clone 2-17)"

( i i i ) HYPOTHETICAL: NO ( i v ) ANTI-SENSE: NO ( v i ) ORIGINAL SOURCE:
        ( A ) ORGANISM: Banana Bunchy Top Virus (BBTV)

( x i ) SEQUENCE DESCRIPTION: SEQ ID NO:4:

```
TATATAAGGA GGAGCGGCTA GTATTACCCG CTCCTCCTCG CACTTCCTCC TCGCACCTGA       60
CGTCATCATT ATGTCCTCTT TTAAATGGTG CTTCACTCTG AATTATTCCT CCGCAGCGGA      120
GCGAGAAGAC TTTCTCGCTC TTCTGAAGGA GGAGGATGTT CACTACTCTG TCGTCGGCGA      180
CGAAGTCGCT CCGGCCACCG GCCAGAAGCA CCTCCAGGGA TATCTATCCC TGAAAAAATC      240
AATTCGCCTC GGCGGATTGA AAAAGAAGTA TGGCTCCCGT GCTCACTGGG AGATTGCGAA      300
AGGAAGTGAC GAACAGAATC GCAGATACTG TTCGAAGGAA ACCCTAGTTC TTGAACTGGG      360
TACTCCGGTG GTTCCTGGTT CGAAGAAGCG CAAGCTTCTC GATAGATTCA GAGAGAGCCC      420
TGAGGAATTG AAGATGGACG ATCCATCCAA GTATCGCAGA TGCTTGGCAG TGGAATCAAT      480
TAAAGATGCC AGAATTAATT CCGAATGGGT TCACGAACTA AAAGAATGGC AAAATAAATT      540
AATTCAACAC ATCGAAGGTG TTCCTGATGA TCGAAGTATC ATCTGGGTAT ACGGTCCCAA      600
CGGAGGCGAA GGAAAGTCAA CCTTCGCAAG ATATCTATCA TTAAAACCCG GATGGGGATA      660
TATCAACGGT GGAAAGACGT CGGATATGAT GCACATCATA ACGATGGATC CTGATAATCA      720
TTGGATTATT GATATCCCCA GAAGTCATTC AGATTATCTG AATTATGGCG TTATAGAACA      780
AATTAAGAAT AGAGTTTTAA TAAATACAAA ATACGAACCA TGTGTGATTA GAAAAGATGG      840
ACAAAATGTC CATGTAATTG TTATGGCAAA TGTGTTGCCT GATTATTGTA AAATTTCAGA      900
AGATAGAATA AAAATAATTA ATTGTTGAGA AAGGAAACTT CCTCCGCAAG CAATCAAAAA      960
GCACGTGGAC CCCACACGGT AGCTTGCAGA ACACGCTATC ATTAAATGCA TCAGAAAATC     1020
ATTATAATTA ATAAATCTCT TATTGGGCCG CAGGCCCATG TAAGGCCCAT TACTTAATGG     1080
GCCGACCTCC TCGCAC                                                    1096
```

( 2 ) INFORMATION FOR SEQ ID NO:5:

( i ) SEQUENCE CHARACTERISTICS:
        ( A ) LENGTH: 1091 base pairs
        ( B ) TYPE: nucleic acid
        ( C ) STRANDEDNESS: single
        ( D ) TOPOLOGY: circular ( i i ) MOLECULE TYPE: subgenomic DNA
        ( A ) DESCRIPTION: /desc "BBTV DNA II (clone 2)"

( i i i ) HYPOTHETICAL: NO ( i v ) ANTI-SENSE: NO ( v i ) ORIGINAL SOURCE:
        ( A ) ORGANISM: Banana Bunchy Top Virus (BBTV)

( x i ) SEQUENCE DESCRIPTION: SEQ ID NO:5:

```
TATATAAGGA  GGAGCGCCTA  GTATTACCCG  CTCCTCCTCG  CCTTTCCTCC  TCGCCCCTGA      60
CGTCATCATT  ATGTCCTCTT  TTAAATGGTG  CTTCACTCTG  AATTATTCCT  CCGCAGCGGA     120
GCGAGAAGAC  TTTCTCGCTC  TTCTGAAGGA  GGAAGAGTTA  AATTACGCTG  TCGTCGGCGA     180
CGAAGTCGCT  CCGAGCACCG  GTCGGAAGCA  CCTCCAGGGA  TATCTATCCC  TGAAGAAATC     240
TATTAAGCTT  GGTGGATTGA  AGAAGAGGTA  CTCTTCGAAG  GCTCACTGGG  AGAGGGCGAG     300
AGGAACTGAT  GAACAGAATC  GCAGATACTG  TTCGAAGGAA  ACCCCTTGAA  CTGGGTACTC     360
CGGTGGTTCC  TGGTTCGAAG  AAGCGCAAGC  TTCTCGATAG  ATTCAGAGAG  AGCCCTGAGG     420
AATTGAAGAT  GGACGATCCA  TCCAAGTATC  GCAGATGCTT  GGCAGTGGAA  TCAATTAAAG     480
ATGCCAGAAT  TAATTCCGAA  TGGGTTCACG  AACTAAAAGA  ATGGCAAAAT  AAATTAATTC     540
AACACATCGA  AGGTGTTCCT  GATGATCGAA  GTATCATCTG  GGTATACGGT  CCTGCCGGAG     600
GCGAAGGAAA  GTCAACCTTC  GCAAGATATC  TATCATTAAA  ACCTGGATGG  GGATATATCA     660
ACGGTGGAAA  GACGTCGGAT  ATGATGCACA  TCATAACGAT  GGATCCTGAT  AATCATTGGA     720
TTATTGATAT  CCCCAGAAGT  CATTCAGATT  ATCTGAATTA  TGGCGTTATA  GAACAAATTA     780
AGAATAGAGT  TTTAATAAAT  ACAAAATACG  AACCATGTGT  GATTAGAAAA  GATGGACAAA     840
ATGTCCATGT  AATTGTTATG  GCAAATGTGT  TGCCTGATTA  TTGTAAAATT  TCAGAAGATA     900
GAATAAAAAT  AATTAATTGT  TGAGAAAGGA  AACTTCCTCC  GCAAGCAATC  AAAAAGCACG     960
TGGACCCCAC  ACGGTAGCTT  GCAGAACACG  CTATCATTAA  ATGCATCAGA  AAATCATTAT    1020
AATTAATAAA  TCTCTTATTG  GGCCGCAGGC  CCATGTAAGG  CCCATTACTT  AATGGGCCGA    1080
CCTCCTCGCC  C                                                            1091
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc= "oligonucleotide primer BB-1"

( i v ) ANTI-SENSE: YES ( x i ) SEQUENCE DESCRIPTION: SEQ ID NO:6:

```
CATGGTCTAT  CGAGGCAAGG                                                      20
```

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc= "oligonucleotide primer BB-3"

( i v ) ANTI-SENSE: NO ( x i ) SEQUENCE DESCRIPTION: SEQ ID NO:7:

GCAGATTCAA TTGACGGAGG    20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc= "oligonucleotide primer 2-2"

( i v ) ANTI-SENSE: NO ( x i ) SEQUENCE DESCRIPTION: SEQ ID NO:8:

ACCACCGGAG TACCCAGTTC    20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc= "oligonucleotide primer 2-3"

( i v ) ANTI-SENSE: NO ( x i ) SEQUENCE DESCRIPTION: SEQ ID NO:9:

TCCTGGTTCG AAGAAGCGCA    20

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc= "oligonucleotide primer C1"

( i v ) ANTI-SENSE: NO ( x i ) SEQUENCE DESCRIPTION: SEQ ID NO:10:

TGGTGCTTCA CTCTGAATTA CTCCTCCGCG    30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc= "oligonucleotide primer C2"

(i v) ANTI-SENSE: NO (x i) SEQUENCE DESCRIPTION: SEQ ID NO:11:

CGCGGAGGAG TAATTCAGAG TGAAGCACCA 30

(2) INFORMATION FOR SEQ ID NO:12:

(i) SEQUENCE CHARACTERISTICS:
    (A) LENGTH: 16 base pairs
    (B) TYPE: nucleic acid
    (C) STRANDEDNESS: both
    (D) TOPOLOGY: linear (i i) MOLECULE TYPE: other nucleic acid
    (A) DESCRIPTION: /desc= "oligonucleotide primer BB-2"

(i v) ANTI-SENSE: NO (x i) SEQUENCE DESCRIPTION: SEQ ID NO:12:

CGAGATTCAA GACGGA 16

(2) INFORMATION FOR SEQ ID NO:13:

(i) SEQUENCE CHARACTERISTICS:
    (A) LENGTH: 11 base pairs
    (B) TYPE: nucleic acid
    (C) STRANDEDNESS: single
    (D) TOPOLOGY: linear (i i) MOLECULE TYPE: other nucleic acid (i v) ANTI-SENSE: NO (x i) SEQUENCE DESCRIPTION: SEQ ID NO:13:

CTTAGTATTA C 11

(2) INFORMATION FOR SEQ ID NO:14:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (i i) MOLECULE TYPE: other nucleic acid (i v) ANTI-SENSE: NO (x i) SEQUENCE DESCRIPTION: SEQ ID NO:14:

AGGAGGAGCG 10

(2) INFORMATION FOR SEQ ID NO:15:

(i) SEQUENCE CHARACTERISTICS:
    (A) LENGTH: 12 base pairs
    (B) TYPE: nucleic acid
    (C) STRANDEDNESS: single
    (D) TOPOLOGY: circular (i i) MOLECULE TYPE: other nucleic acid (i v) ANTI-SENSE: NO (x i) SEQUENCE DESCRIPTION: SEQ ID NO:15:

CCTAGTATTA CC 12

(2) INFORMATION FOR SEQ ID NO:16:

(i) SEQUENCE CHARACTERISTICS:

(A) LENGTH: 286 amino acids
(B) TYPE: amino acid
(D) TOPOLOGY: linear (ii) MOLECULE TYPE: protein
(A) DESCRIPTION:/desc="DNA I- V1"

(xi) SEQUENCE DESCRIPTION: SEQ ID NO:16:

| Met | Ser | Ser | Pro | Ser | Leu | Lys | Trp | Cys | Phe | Thr | Leu | Asn | Tyr | Ser | Ser |
|---|---|---|---|---|---|---|---|---|---|---|---|---|---|---|---|
| 1 | | | | 5 | | | | | 10 | | | | | 15 | |
| Ala | Ala | Glu | Arg | Glu | Asn | Phe | Leu | Ser | Leu | Leu | Lys | Glu | Glu | Asp | |
| | | | 20 | | | | 25 | | | | 30 | | | | |
| Val | His | Tyr | Ala | Val | Val | Gly | Asp | Glu | Val | Ala | Pro | Ala | Thr | Gly | |
| | | | 35 | | | | 40 | | | | | | 45 | | |
| Gln | Lys | His | Leu | Gln | Gly | Tyr | Leu | Ser | Leu | Lys | Lys | Arg | Ile | Arg | |
| | | | 50 | | | | | 55 | | | | | 60 | | |
| Leu | Gly | Gly | Leu | Lys | Lys | Lys | Tyr | Gly | Ser | Arg | Ala | His | Trp | Glu | |
| | | | 65 | | | | | 70 | | | | | 75 | | |
| Ile | Ala | Arg | Gly | Thr | Asp | Glu | Glu | Asn | Ser | Lys | Tyr | Cys | Ser | Lys | |
| | | | 80 | | | | | 85 | | | | | 90 | | |
| Gly | Thr | Leu | Ile | Leu | Glu | Leu | Gly | Phe | Pro | Val | Val | Asn | Gly | Ser | |
| | | | 95 | | | | | 100 | | | | | 105 | | |
| Asn | Lys | Arg | Lys | Ile | Ser | Glu | Met | Val | Ala | Arg | Ser | Pro | Asp | Arg | |
| | | | 110 | | | | | 115 | | | | | 120 | | |
| Met | Lys | Ile | Glu | Gln | Pro | Glu | Ile | Phe | His | Arg | Tyr | Gln | Ser | Val | |
| | | | 125 | | | | | 130 | | | | | 135 | | |
| Asn | Lys | Leu | Lys | Lys | Phe | Lys | Glu | Glu | Phe | Val | His | Pro | Cys | Leu | |
| | | | 140 | | | | | 145 | | | | | 150 | | |
| Asp | Ser | Pro | Trp | Gln | Ile | Gln | Leu | Thr | Glu | Ala | Ile | Asp | Glu | Glu | |
| | | | 155 | | | | | 160 | | | | | 165 | | |
| Pro | Asp | Asp | Arg | Ser | Ile | Ile | Trp | Val | Tyr | Gly | Pro | Tyr | Gly | Asn | |
| | | | 170 | | | | | 175 | | | | | 180 | | |
| Glu | Gly | Lys | Ser | Thr | Tyr | Ala | Lys | Ser | Leu | Ile | Lys | Lys | Asp | Trp | |
| | | | 185 | | | | | 190 | | | | | 195 | | |
| Phe | Tyr | Thr | Arg | Gly | Gly | Lys | Lys | Glu | Asn | Ile | Leu | Phe | Ser | Tyr | |
| | | | 200 | | | | | 205 | | | | | 210 | | |
| Val | Asp | Glu | Gly | Ser | Asp | Lys | His | Ile | Val | Phe | Asp | Ile | Pro | Arg | |
| | | | 215 | | | | | 220 | | | | | 225 | | |
| Cys | Asn | Gln | Asp | Tyr | Leu | Asn | Tyr | Asp | Val | Ile | Glu | Ala | Leu | Lys | |
| | | | 230 | | | | | 235 | | | | | 240 | | |
| Asp | Arg | Val | Ile | Glu | Ser | Thr | Lys | Tyr | Lys | Pro | Ile | Lys | Ile | Val | |
| | | | 245 | | | | | 250 | | | | | 255 | | |
| Glu | Leu | Gly | Lys | Ile | His | Val | Ile | Val | Met | Ala | Asn | Phe | Met | Pro | |
| | | | 260 | | | | | 265 | | | | | 270 | | |
| Asp | Phe | Cys | Lys | Ile | Ser | Glu | Asp | Arg | Ile | Lys | Ile | Ile | Tyr | Cys | |
| | | | 275 | | | | | 280 | | | | | 285 | | |

(2) INFORMATION FOR SEQ ID NO:17:

(i) SEQUENCE CHARACTERISTICS:
(A) LENGTH: 285 amino acids
(B) TYPE: amino acid
(D) TOPOLOGY: linear (ii) MOLECULE TYPE: protein
(A) DESCRIPTION:/desc="DNA II V2 (D2)"

(xi) SEQUENCE DESCRIPTION: SEQ ID NO:17:

Met Ser Ser Phe Lys Trp Cys Phe Thr Leu Asn Tyr Ser Ser Ala Ala

|   | 1 |   |   |   | 5 |   |   |   |   | 10 |   |   |   |   | 15 |
|---|---|---|---|---|---|---|---|---|---|----|---|---|---|---|----|
| Glu | Arg | Glu | Asp 20 | Phe | Leu | Ala | Leu | Leu 25 | Lys | Glu | Glu | Asp | Val 30 | His |
| Tyr | Ser | Val | Val 35 | Gly | Asp | Glu | Val | Ala 40 | Pro | Ala | Thr | Gly | Gln 45 | Lys |
| His | Leu | Gly | Gly 50 | Tyr | Leu | Ser | Leu | Lys 55 | Lys | Ser | Ile | Arg | Leu 60 | Gly |
| Gly | Leu | Lys | Lys 65 | Lys | Tyr | Gly | Ser | Arg 70 | Ala | His | Trp | Glu | Ile 75 | Ala |
| Lys | Gly | Ser | Asp 80 | Glu | Gln | Asn | Arg | Arg 85 | Tyr | Cys | Ser | Lys | Glu 90 | Thr |
| Leu | Val | Leu | Glu 95 | Leu | Gly | Thr | Pro | Val 100 | Val | Pro | Gly | Ser | Lys 105 | Lys |
| Arg | Lys | Leu | Leu 110 | Asp | Arg | Phe | Arg | Glu 115 | Ser | Pro | Glu | Glu | Leu 120 | Lys |
| Met | Asp | Asp | Pro 125 | Ser | Lys | Tyr | Arg | Arg 130 | Cys | Leu | Ala | Val | Glu 135 | Ser |
| Ile | Lys | Asp | Ala 140 | Arg | Ile | Asn | Ser | Glu 145 | Trp | Val | His | Glu | Leu 150 | Lys |
| Glu | Trp | Gln | Asn 155 | Lys | Leu | Ile | Gln | His 160 | Ile | Glu | Gly | Val | Pro 165 | Asp |
| Asp | Arg | Ser | Ile 170 | Ile | Trp | Val | Tyr | Gly 175 | Pro | Asn | Gly | Gly | Glu 180 | Gly |
| Lys | Ser | Thr | Phe 185 | Ala | Arg | Tyr | Leu | Ser 190 | Leu | Lys | Pro | Gly | Trp 195 | Gly |
| Tyr | Ile | Asn | Gly 200 | Gly | Lys | Thr | Ser | Asp 205 | Met | Met | His | Ile | Ile 210 | Thr |
| Met | Asp | Pro | Asp 215 | Asn | His | Trp | Ile | Ile 220 | Asp | Ile | Pro | Arg | Ser 225 | His |
| Ser | Asp | Tyr | Leu 230 | Asn | Tyr | Gly | Val | Ile 235 | Glu | Gln | Ile | Lys | Asn 240 | Arg |
| Val | Leu | Ile | Asn 245 | Thr | Lys | Tyr | Glu | Pro 250 | Cys | Val | Ile | Arg | Lys 255 | Asp |
| Gly | Gln | Asn | Val 260 | His | Val | Ile | Val | Met 265 | Ala | Asn | Val | Leu | Pro 270 | Asp |
| Tyr | Cys | Lys | Ile 275 | Ser | Glu | Asp | Arg | Ile 280 | Lys | Ile | Ile | Asn | Cys 285 |   |

(2) INFORMATION FOR SEQ ID NO:18:

(i) SEQUENCE CHARACTERISTICS:
        (A) LENGTH: 286 amino acids
        (B) TYPE: amino acid
        (D) TOPOLOGY: linear (ii) MOLECULE TYPE: protein
        (A) DESCRIPTION:/desc="DNA II V2 C1"

(xi) SEQUENCE DESCRIPTION: SEQ ID NO:18:

| Met 1 | Ala | Arg | Tyr | Val 5 | Val | Cys | Trp | Met | Phe 10 | Thr |
|---|---|---|---|---|---|---|---|---|---|---|
| Ile | Asn | Asn | Pro 15 | Thr | Thr | Leu | Pro | Val 20 | Met | Arg | Asp | Glu | Ile 25 | Lys |
| Tyr | Lys | Val | Tyr 30 | Gln | Val | Asp | Arg | Gly 35 | Gln | Glu | Gly | Thr | Arg 40 |   |
| His | Val | Gln | Gly 45 | Tyr | Val | Glu | Met | Lys 50 | Arg | Arg | Ser | Ser | Leu 55 | Lys |

| | | | | | | | | | | | | | | |
|---|---|---|---|---|---|---|---|---|---|---|---|---|---|---|
| Gln | Met | Arg | Gly | Phe<br>60 | Phe | Pro | Gly | Ala | His<br>65 | Leu | Glu | Lys | Arg | Lys<br>70 |
| Gly | Ser | Gln | Glu | Glu<br>75 | Ala | Arg | Ser | Tyr | Cys<br>80 | Met | Lys | Glu | Asp | Thr<br>85 |
| Arg | Ile | Glu | Gly | Pro<br>90 | Glu | Glu | Phe | Gly | Ser<br>95 | Phe | Lys | Leu | Ser | Cys<br>100 |
| Asn | Asp | Asn | Leu | Phe<br>105 | Asp | Val | Ile | Gln | Asp<br>110 | Met | Arg | Glu | Thr | His<br>115 |
| Lys | Arg | Pro | Leu | Glu<br>120 | Tyr | Leu | Tyr | Asp | Cys<br>125 | Pro | Asn | Thr | Phe | Asp<br>130 |
| Arg | Ser | Lys | Asp | Thr<br>135 | Leu | Tyr | Arg | Val | Gln<br>140 | Ala | Glu | Met | Asn | Lys<br>145 |
| Thr | Lys | Ala | Met | Asn<br>150 | Ser | Trp | Arg | Thr | Ser<br>155 | Phe | Ser | Ala | Trp | Thr<br>160 |
| Ser | Glu | Val | Glu | Asn<br>165 | Val | Met | Ala | Gln | Pro<br>170 | Cys | His | Arg | Arg | Ile<br>175 |
| Ile | Trp | Val | Tyr | Gly<br>180 | Pro | Asn | Gly | Gly | Glu<br>185 | Gly | Lys | Thr | Thr | Tyr<br>190 |
| Ala | Lys | His | Leu | Met<br>195 | Lys | Thr | Arg | Asn | Ala<br>200 | Phe | Tyr | Ser | Pro | Gly<br>205 |
| Gly | Lys | Ser | Leu | Asp<br>210 | Ile | Cys | Arg | Leu | Tyr<br>215 | Asn | Tyr | Glu | Asp | Ile<br>220 |
| Val | Ile | Phe | Asp | Ile<br>225 | Pro | Arg | Cys | Lys | Glu<br>230 | Asp | Tyr | Leu | Asn | Tyr<br>235 |
| Gly | Leu | Leu | Glu | Glu<br>240 | Phe | Lys | Asn | Gly | Ile<br>245 | Ile | Gln | Ser | Gly | Lys<br>250 |
| Tyr | Glu | Pro | Val | Leu<br>255 | Lys | Ile | Val | Gly | Tyr<br>260 | Val | Glu | Val | Ile | Val<br>265 |
| Met | Ala | Asn | Phe | Leu<br>270 | Pro | Lys | Glu | Gly | Ile<br>275 | Phe | Ser | Glu | Asp | Arg Ile<br>280 |
| Lys | Leu | Val | Ser | Cys<br>285 | | | | | | | | | | |

What is claimed is:

1. An isolated DNA molecule comprising a nucleotide sequence encoding a polypeptide comprising amino acid sequence SEQ ID NO: 16, wherein said sequence is selected from the group consisting of:
   (a) nucleotide sequence SEQ ID NO: 3;
   (b) fragments of nucleotide sequence SEQ ID NO: 3 that selectively hybridize to Banana Bunchy Top Virus (BBTV) DNA; and
   (c) nucleotide sequences which, as a result of the aenetic code, are degenerate to the sequences of (a) or (b).

2. An isolated DNA molecule comprising a nucleotide sequence encoding a polypeptide comprising amino acid sequence SEQ ID NO: 17, wherein said sequence is selected from the group consisting of:
   (a) nucleotide sequence SEQ ID NO: 4;
   (b) fragments of nucleotide sequence SEQ ID NO. 4 that selectively hybridize to Banana Bunchy Top Virus (BBTV) DNA; and
   (c) nucleotide sequences which, as a result of the aenetic code, are degenerate to the sequences of (a) or (b).

3. An isolated polypeptide, wherein said polypeptide is encoded by an open reading frame in a nucleotide sequence which is a subsequence of the Banana Bunchy Top Virus (BBTV) genome, said nucleotide sequence being nucleotide sequence SEQ ID NO: 3, or a nucleotide sequence which, as a result of the genetic code, is degenerate thereto.

4. An isolated polyoeptide, wherein said polypeptide is encoded by an open reading frame in a nucleotide sequence which is a subsequence of the Banana Bunchy Top Virus (BBTV) genome, said nucleotide sequence being nucleotide sequence SEQ ID NO: 4, or a nucleotide sequence which, as a result of the genetic code, is degenerate thereto.

5. The isolated protein of claim 4, wherein said protein is a replicase.

6. An isolated DNA molecule comprising a nucleotide sequence encoding a fragment of a component of the Banana Bunchy Top Virus (BBTV) genome, wherein said sequence is selected from the group consisting of:
   (a) nucleotide sequence SEQ ID NO. 1
   (b) fragments of nucleotide sequence SEQ ID NO. 1 that selectively hybridize to Banana Bunchy Top Virus (BBTV) DNA; and
   (c) nucleotide sequences which are degenerate to the sequences of (a) or (b).

7. A method for detecting Banana Bunchy Top Virus (BBTV) in plant tissues comprising the steps of:
   (a) extracting the total DNA of the plant tissues or the DNA of viruses contained in the plant tissues;

(b) selecting an inversely oriented primer pair from the group consisting of SEQ ID NO: 1, SEQ ID NO: 2, SEQ ID NO: 3 and SEQ ID NO: 4;

(c) performing polymerase chain reaction (PCR) using the extracted DNA as template and the selected primer pair to obtain a PCR product; and (d) determining the size of the PCR product obtained, wherein a DNA fragment of 1.1 Kb is indicative of the presence of BBTV in the plant tissues.

8. The method of claim 7 wherein the plant is a banana plant.

9. The method of claim 8 wherein the banana plant is *Musa sp.*

10. The method of claim 8 wherein the selected primer pair is selected from the group consisting of:

(a) CATGGTCTATCGAGGCAAGG (SEQ ID NO: 6) and GCAGATTCAATTGACGGAGG (SEQ ID NO: 7);

(b) CATGGTCTATCGAGGCAAGG (SEQ ID NO: 6) and CGAGATTCAAGACGGA (SEQ ID NO: 12); and (c) ACCACCGGAGTACCCAGTTC (SEQ ID NO: 8) and TCCTGGTTCGAAGAAGCGCA (SEQ ID NO: 9).

11. The polypeptide of claim 3 wherein said polypeptide comprises amino acid sequence SEQ ID NO: 16.

12. The polypeptide of claim 4 wherein said polypeptide comprises amino acid sequence SEQ ID NO: 17.

* * * * *